United States Patent
Hawkes et al.

(10) Patent No.: US 11,944,552 B2
(45) Date of Patent: Apr. 2, 2024

(54) STAND-ALONE INTERBODY FUSION

(71) Applicant: Nexus Spine, L.L.C., Salt Lake City, UT (US)

(72) Inventors: David Hawkes, Pleasant Grove, UT (US); Peter Halverson, Draper, UT (US); Jeffrey Ellis Harris, Holladay, UT (US); Jeffrey S. Hoskins, Waynesville, OH (US)

(73) Assignee: Nexus Spine, LLC, Salt Lake City, UT (US)

( * ) Notice: Subject to any disclaimer, the term of this patent is extended or adjusted under 35 U.S.C. 154(b) by 75 days.

(21) Appl. No.: 16/297,290

(22) Filed: Mar. 8, 2019

(65) Prior Publication Data
US 2019/0274841 A1    Sep. 12, 2019

Related U.S. Application Data

(60) Provisional application No. 62/640,556, filed on Mar. 8, 2018, provisional application No. 62/689,703, filed
(Continued)

(51) Int. Cl.
*A61F 2/44* (2006.01)
*A61F 2/30* (2006.01)
*A61F 2/46* (2006.01)

(52) U.S. Cl.
CPC ........ *A61F 2/4455* (2013.01); *A61F 2/30749* (2013.01); *A61F 2/442* (2013.01);
(Continued)

(58) Field of Classification Search
CPC .......... A61F 2/44; A61F 2/442; A61F 2/4455; A61F 2/447; A61F 2/4611;
(Continued)

(56) References Cited

U.S. PATENT DOCUMENTS 3,867,728 A    2/1975  Stubstad et al.
5,702,391 A *  12/1997  Lin ......................... A61F 2/446
                                                         623/17.11
(Continued)

FOREIGN PATENT DOCUMENTS

WO    2011143219 A1    11/2011

OTHER PUBLICATIONS

KIPO—International Search Report/Written Opinion from related case PCT/US2019/021461.

*Primary Examiner* — Eric S Gibson
(74) *Attorney, Agent, or Firm* — Bryant J. Keller; Kirton McConkie

(57) ABSTRACT

Improved fixation or stabilization of implants is achieved via one or more deployable spikes or anchors. The deployable spikes or anchors may be present in the implant in a nested, collapsed, or retracted position while the implant is inserted into the human body, and may then be deployed (e.g., into adjacent bone) after the implant is in place, thereby fixing the implant's location against unwanted movement. Such fixation or stabilization of the implant may reduce patients' pain, may improve overall short-term and long-term stability of the implant, and may improve osteo-integration into the implant.

20 Claims, 15 Drawing Sheets

Related U.S. Application Data on Jun. 25, 2018, provisional application No. 62/689,707, filed on Jun. 25, 2018.

(52) U.S. Cl.
CPC ..... *A61F 2/4611* (2013.01); *A61F 2002/3028* (2013.01); *A61F 2002/30579* (2013.01); *A61F 2002/30593* (2013.01); *A61F 2002/30622* (2013.01); *A61F 2002/30845* (2013.01); *A61F 2002/30892* (2013.01)

(58) Field of Classification Search
CPC .. A61F 2002/30579; A61F 2002/30841; A61F 2002/30845; A61F 2002/30891; A61F 2002/30892
See application file for complete search history.

(56) References Cited

U.S. PATENT DOCUMENTS

| | | | | |
|---|---|---|---|---|
| 5,800,547 | A * | 9/1998 | Schafer | A61F 2/442 623/17.16 |
| 5,800,550 | A * | 9/1998 | Sertich | A61F 2/447 623/17.16 |
| 6,179,873 | B1 * | 1/2001 | Zientek | A61F 2/4657 623/17.11 |
| 6,371,987 | B1 * | 4/2002 | Weiland | A61F 2/4455 623/17.11 |
| 6,527,803 | B1 * | 3/2003 | Crozet | A61F 2/442 623/17.11 |
| 6,767,367 | B1 * | 7/2004 | Michelson | A61F 2/447 623/17.16 |
| 7,309,357 | B2 | 12/2007 | Kim | |
| 7,517,228 | B2 | 4/2009 | Baskaran et al. | |
| 7,604,870 | B2 | 10/2009 | Chemyshov et al. | |
| 7,704,279 | B2 * | 4/2010 | Moskowitz | A61B 17/7064 623/17.11 |
| 7,846,188 | B2 * | 12/2010 | Moskowitz | A61B 17/068 606/279 |
| 8,062,374 | B2 * | 11/2011 | Markworth | A61F 2/447 623/17.16 |
| 8,070,812 | B2 * | 12/2011 | Keller | A61F 2/44 623/17.11 |
| 8,257,443 | B2 * | 9/2012 | Kamran | A61F 2/4465 623/17.16 |
| 8,425,528 | B2 * | 4/2013 | Berry | A61F 2/447 606/99 |
| 8,512,409 | B1 * | 8/2013 | Mertens | A61F 2/447 623/17.16 |
| 8,523,946 | B1 * | 9/2013 | Swann | A61F 2/4455 623/17.16 |
| 8,545,563 | B2 * | 10/2013 | Brun | A61F 2/447 623/17.11 |
| 8,597,360 | B2 * | 12/2013 | McLuen | A61F 2/44 623/17.16 |
| 8,685,104 | B2 * | 4/2014 | Lee | A61F 2/4465 623/17.16 |
| 8,998,920 | B2 * | 4/2015 | Berry | A61F 2/447 606/99 |
| 9,138,331 | B2 * | 9/2015 | Aferzon | A61B 17/864 |
| 9,517,144 | B2 * | 12/2016 | McAtamney | A61F 2/30749 |
| 9,707,100 | B2 * | 7/2017 | Duffield | A61F 2/4611 |
| 9,763,804 | B1 * | 9/2017 | Huang | A61F 2/447 |
| 9,877,842 | B2 * | 1/2018 | Chataigner | A61F 2/4611 |
| 9,918,849 | B2 | 3/2018 | Morris et al. | |
| 9,925,059 | B2 * | 3/2018 | Chataigner | A61F 2/4611 |
| 9,949,846 | B2 * | 4/2018 | Duffield | A61F 2/4611 |
| 10,022,246 | B2 * | 7/2018 | Mackenzie | A61F 2/442 |
| 10,137,005 | B2 * | 11/2018 | Ashleigh | A61F 2/447 |
| 10,307,265 | B2 * | 6/2019 | Sack | A61F 2/4465 |
| 10,405,992 | B2 * | 9/2019 | Sack | A61F 2/4455 |
| 10,449,060 | B2 * | 10/2019 | Sack | A61F 2/4455 |
| 10,849,758 | B2 * | 12/2020 | Rathbun | A61F 2/30771 |
| 2002/0128714 | A1 | 9/2002 | Manasas et al. | |
| 2003/0109928 | A1 * | 6/2003 | Pasquet | A61F 2/4611 623/17.11 |
| 2005/0033429 | A1 * | 2/2005 | Kuo | A61F 2/447 623/17.11 |
| 2005/0049590 | A1 * | 3/2005 | Alleyne | A61F 2/442 623/17.11 |
| 2006/0069436 | A1 * | 3/2006 | Sutton | A61F 2/4684 623/17.13 |
| 2006/0095136 | A1 * | 5/2006 | McLuen | A61F 2/4455 623/23.47 |
| 2007/0049943 | A1 * | 3/2007 | Moskowitz | A61F 2/4611 606/279 |
| 2007/0270960 | A1 * | 11/2007 | Bonin, Jr. | A61F 2/4611 623/17.11 |
| 2007/0270961 | A1 * | 11/2007 | Ferguson | A61F 2/44 623/17.11 |
| 2008/0027550 | A1 * | 1/2008 | Link | A61B 17/1671 623/17.16 |
| 2008/0051901 | A1 * | 2/2008 | de Villiers | A61F 2/4425 623/17.16 |
| 2008/0051902 | A1 * | 2/2008 | Dwyer | A61F 2/442 623/17.16 |
| 2008/0147098 | A1 | 6/2008 | Trieu | |
| 2009/0099601 | A1 * | 4/2009 | Aferzon | A61F 2/4455 606/246 |
| 2009/0265007 | A1 | 10/2009 | Colleran | |
| 2010/0137990 | A1 | 6/2010 | Apatsidis | |
| 2010/0161057 | A1 * | 6/2010 | Berry | A61F 2/4465 623/17.16 |
| 2010/0185289 | A1 * | 7/2010 | Kirwan | A61F 2/4455 623/17.11 |
| 2011/0178599 | A1 * | 7/2011 | Brett | A61F 2/4465 623/17.16 |
| 2011/0208311 | A1 * | 8/2011 | Janowski | A61F 2/4611 623/17.16 |
| 2011/0208312 | A1 * | 8/2011 | Moskowitz | A61B 17/7064 623/17.16 |
| 2012/0022654 | A1 * | 1/2012 | Farris | A61F 2/4611 623/17.16 |
| 2012/0029644 | A1 * | 2/2012 | Markworth | A61F 2/447 623/17.16 |
| 2012/0197404 | A1 * | 8/2012 | Brun | A61F 2/4611 623/17.16 |
| 2012/0277867 | A1 * | 11/2012 | Kana | A61F 2/4465 623/17.16 |
| 2013/0110242 | A1 | 5/2013 | Kirwan et al. | |
| 2013/0150969 | A1 * | 6/2013 | Zipnick | A61B 17/320016 623/17.16 |
| 2013/0245767 | A1 * | 9/2013 | Lee | A61F 2/442 623/17.16 |
| 2013/0310935 | A1 * | 11/2013 | Swann | A61F 2/4455 623/17.11 |
| 2013/0338776 | A1 * | 12/2013 | Jones | A61F 2/4611 623/17.16 |
| 2014/0100662 | A1 * | 4/2014 | Patterson | A61F 2/4455 623/17.16 |
| 2015/0018952 | A1 * | 1/2015 | Ali | A61F 2/442 623/17.15 |
| 2015/0100127 | A1 * | 4/2015 | Bal | A61F 2/447 623/17.16 |
| 2015/0127107 | A1 * | 5/2015 | Kim | A61F 2/4611 623/17.16 |
| 2015/0209089 | A1 * | 7/2015 | Chataigner | A61F 2/4611 623/17.16 |
| 2015/0305880 | A1 * | 10/2015 | Kim | A61F 2/4465 623/17.16 |
| 2015/0305887 | A1 * | 10/2015 | McAtamney | A61F 2/4455 623/17.16 |
| 2015/0320568 | A1 * | 11/2015 | Ameil | A61F 2/4637 623/17.13 |
| 2016/0015526 | A1 * | 1/2016 | Ali | A61F 2/442 623/17.16 |
| 2016/0338851 | A1 | 11/2016 | Ashleigh et al. | |
| 2016/0374831 | A1 * | 12/2016 | Duffield | A61F 2/4455 623/17.16 |

(56) References Cited

U.S. PATENT DOCUMENTS

| | | |
|---|---|---|
| 2017/0095350 A1 | 4/2017 | Brett |
| 2017/0156880 A1* | 6/2017 | Halverson ............. A61F 2/0077 |
| 2017/0165082 A1* | 6/2017 | Faulhaber ............... A61F 2/447 |
| 2017/0266016 A1* | 9/2017 | Faulhaber ............... A61F 2/447 |
| 2017/0304080 A1 | 10/2017 | Lee et al. |
| 2018/0104068 A1* | 4/2018 | Sack ..................... A61F 2/4465 |
| 2018/0110627 A1* | 4/2018 | Sack ..................... A61F 2/4465 |
| 2019/0274841 A1* | 9/2019 | Hawkes ................. A61F 2/442 |
| 2020/0179135 A1* | 6/2020 | Castro ................... A61F 2/4455 |

\* cited by examiner

STAND-ALONE INTERBODY FUSION

CROSS-REFERENCE TO RELATED APPLICATIONS

This application claims the benefit of U.S. Provisional Application No. 62/640,556, filed Mar. 8, 2018, U.S. Provisional Application No. 62/689,703, filed Jun. 25, 2018, and U.S. Provisional Application No. 62/689,707, filed Jun. 25, 2018, each of which is incorporated herein by reference in their entireties for all they disclose.

This application is related to U.S. patent application Ser. No. 15/372,290, filed Dec. 7, 2106, which is incorporated herein by reference for all it discloses.

BACKGROUND OF THE INVENTION

1. Field of the Invention

The present invention relates to spinal fusion implants, and more particularly to a porous interbody spacer having features increasing stabilization of the implants in the disc space.

2. Background and Related Art

Human bones are generally formed of two types of structural bone tissue: cortical bone and trabecular or cancellous bone. Cortical bone generally forms the outer shell of most bones, and is more dense, harder, stronger, and stiffer than trabecular bone. Trabecular bone is typically found at the ends of long bones proximal to joints, as well as in the interior of vertebrae. Trabecular bone is highly vascularized and has a generally porous or spongy structure through which blood vessels pass. Generally, trabecular bone has pores that are on the order of 150 to 650 microns in size. Not all trabecular bone has the same porosity: different bones have different trabecular bone porosity.

The physical characteristics of bone are important for physiological purposes related to the growth and formation of bone both originally as well as during the healing process. The cells responsible for bone growth, including osteocytes and osteoblasts, work together to form bone as needed within the body, but will only form bone under proper conditions, including when the cells experience proper loads and stresses, when a network of blood vessels is available to supply needed nutrients, and when gaps to be filled by bone are of a proper size. When proper conditions are not available, bone cannot or will not grow. For example, when bone does not experience loading, it will not grow and can even be resorbed. Additionally, when gaps to be filled are too large or too small, bone cannot bridge the gap and will not grow.

In addition to proper physical conditions, bone growth only occurs when certain conditions are met. First, there must be a kernel of living bone to start the process. The living bone supplies the cells necessary for bone growth and formation. Additionally, a cascade of chemical triggers is required for bone to grow. Finally, because bone growth is impeded by the presence of certain materials and/or chemicals, an absence of such materials and chemicals is required for proper bone growth.

One example of where it is generally recognized as advantageous to promote bone growth is in the orthopedic implant industry. One goal with many orthopedic implants is for bone growth at the interface to fuse or secure the implant to the bone. For this reason, many orthopedic implants are provided with a porous surface at the bone-implant interface, with the expectation that bone will grow into the porous surface of the implant. Other implants may be provided with one or more cavities or voids to receive bone growth (e.g., a graft window), and during surgery any such cavities or voids may be filled with a material intended to promote bone growth, including morcellized bone graft material. These techniques have been used in implants for years with varying degrees of success, but the success of such devices has been limited by the devices' ongoing failure to provide physical and chemical characteristics most conducive to bone growth. Even when a graft is present in a cavity or void, any bone that does form on or around the device is of lesser quality and quantity.

Generally, current implants have one or more characteristics that are not maximally conducive to facilitating bone growth into the implant. For example, some implants may provide a pore size that is generally within a desirable range, but may have a stiffness that is too high to allow bone within the porous structure of the implant to be properly loaded. As a result, the bone will not take advantage of the correct porosity and pore size of such implants, and will grow only minimally, if at all, in the porous structure of such implants. In other implants, the stiffness may be generally within a desirable range, but in order to achieve the desired stiffness, the device manufacturer creates pores that are too large or too small to facilitate proper bone growth. As a result, while the bone cells can be properly loaded, they are unable to grow bone in the available pores.

Some manufacturers have used the material polyetheretherketone (PEEK) in orthopedic implants, as PEEK has a bulk stiffness (4 gigapascals (GPa)) that is close to that of bone (0.3 GPa<bone stiffness<4 GPa). Unfortunately, PEEK is not chemically a bone-friendly material. As a result, when PEEK is used for implants, a fibrous layer is formed by the body around the implant to protect the body from the PEEK, and bone growth does not occur. Other commonly used materials are titanium and tantalum, which are osteoconductive but have a relatively high bulk stiffness (approximately 116 GPa) that shields the bone from appropriate mechanical stimulus necessary for proper bone growth. Stainless steel, another possible implant material, is not very osteoconductive and also has a very high bulk stiffness (approximately 210 GPa).

Many currently available implants made of titanium have a stiffness that approaches the stiffness of a block of solid titanium. These devices are typically too stiff even in their porous regions. Additionally, many devices have porous regions contained within a solid surrounding structure that prevents the intervening porous region from being loaded in a way conducive to bone growth. Trabecular metal is one of the least stiff predicate materials that is still more than twice as stiff as the maximum desired stiffness desired to promote bone growth through proper loading.

One particular type of implant that is illustrative of the difficulties encountered with predicate devices is an interbody spacer intended for placement between vertebral bodies in spinal fusion procedures. Predicate devices have focused almost exclusively on providing support for the spine, giving little to no attention to promoting or stimulating bone growth. As a result, while such devices may achieve bone on-growth at the surface of the device, such devices do not achieve ingrowth that extends throughout the devices.

For example, the TM-S® cervical fusion device and the TM Ardis® interbody system by Zimmer Biomet are made using elemental tantalum ("trabecular metal") and achieve a pore size on the order of 550 microns. Despite having a pore size that is generally within the desired range, the stiffness of the implant is determined by the size and shape of the material between the pores, and remains at least twice and as much as ten times the desired stiffness. Due to the lack of proper loading, bone does not grow within the Zimmer devices to a significant extent.

Similarly, Stryker's Tritanium® PL posterior lumbar cage has a pore size of 616 microns, only slightly exceeding the desired pore size. Again, however, the device's stiffness is determined by the size and shape of the material between the pores and at the margins of the device itself. As a result, any bone that does enter the pores of the device cannot be properly loaded, and ingrowth does not occur. The stiffness of the Stryker device may exceed the stiffness of the Zimmer devices.

Other devices, such as the 4WEB® Medical Spine Truss system, the K2M Cascadia™ devices, the Titan Endoskeleton® TO device, and the Signus-Mobis® II ST devices all have even larger pore sizes as well as portions of solid non-porous titanium along leading and trailing edges of the devices. Thus, even if portions of such devices have a stiffness that is generally correct, such portions cannot be loaded due to the solid portions of the devices. The lack of loading prevents bone growth in the interior of the devices. Additionally, the large pore sizes (e.g., on the order of greater than 1700 microns) cannot be bridged by bone.

Thus, there remains an unmet need in the orthopedic implant industry for implants that provide stiffness and pore sizes that are conducive to bone growth using materials that are also conducive to bone growth. This need is especially felt in the spinal implant industry, for example with respect to interbody spacers.

Another need in the orthopedic implant industry is a need to fix and stabilize implants after placement and before bone growth onto and into the implant has occurred. Prior to bone ongrowth/ingrowth, it may be possible for the implant to move within the interbody space. Movement of the implant causes instability of the spine and increased pain for the patient. Additionally, the movement of the implant may prevent bone ongrowth/ingrowth from occurring or may reduce bone ongrowth/ingrowth. In particularly bad cases, the implant may migrate from a desired placement location, which may require revision.

Existing fixation options are limited. Some fixation options currently used include one or more teeth protruding from cranial and/or caudal surfaces of the implant in an attempt to prevent or reduce the possibility of the implant migrating anteriorly after, for example, a direct anterior placement procedure. In some instances, further fixation mechanisms may be used. Some of such mechanisms may protrude anteriorly of the implant after fixation. Other mechanisms may require screw placement at oblique and challenging angles. One attempt to address some of these concerns is the ROI-A ALIF cage by Zimmer Biomet, in which self-guided curved "VerteBRIDGE" plating is delivered in the plane of the disc and then curve cranially and caudally into the adjacent vertebral bodies. A problem with the ROI-A device, however, is that the curved plates may interfere with similar curved plates of adjacent implants in multi-level fusion procedures. Additionally, the curved nature of the plate leaves more potential for movement than would a fixation mechanism oriented more in-line with the spine (e.g., more orthogonal to the vertebral bodies). Accordingly, there are ongoing difficulties with existing

BRIEF SUMMARY OF THE INVENTION

Embodiments of the invention provide improved fixation or stabilization of implants via one or more deployable spikes or anchors. The deployable spikes or anchors may be present in the implant in a nested, collapsed, or retracted position while the implant is inserted into the human body, and may then be deployed (e.g., into adjacent bone) after the implant is in place, thereby fixing the implant's location against unwanted movement. Such fixation or stabilization of the implant may reduce patients' pain, may improve overall short-term and long-term stability of the implant, and may improve osteo-integration into the implant.

The one or more deployable spikes or anchors of embodiments of the implant differ from traditional fixation systems in several regards. First, the deployable spikes or anchors are contained within the implant during the implant insertion procedure, and there is no need to later add a separate fixation device such as a screw or other anchor, and there is therefore no need for tools or implements that can secure and manipulate such a separate fixation device as it is brought to and added to the implant in-situ. Additionally, the deployable spikes or anchors move largely perpendicular to a general plane of symmetry of the implant, and therefore move into and anchor the implant in the adjacent bone in a direction generally orthogonal to an insertion direction taken by the implant during insertion. Accordingly, deployment of the deployable spikes or anchors better secures the implant against unwanted motion than do traditional anchoring devices that are inserted at angles other than generally orthogonal. Furthermore, the deployable spikes or anchors may be deployed using a simple manipulation of an anchor-deployment tool from a direct-anterior position after the implant is placed. This simple manipulation step minimizes the steps necessary for anchoring, minimizes forces applied to the implant after implant placement, and makes for extremely easy implant fixation or stabilization. Manipulation of the anchor-deployment tool can occur while an implant-insertion tool remains engaged with the implant, ensuring that proper implant placement is maintained while the deployable spikes or anchors are deployed.

An additional difference of the deployable spikes or anchors of the implant is that the deployable spikes or anchors may be returned to the nested, collapsed, or retracted position in the event a revision surgery becomes necessary. Accordingly, removal of the implant becomes much easier than with traditional implant fixation systems, as traditional fixation systems may require significant destruction of surrounding bony structures to obtain removal of the implant with its traditional fixation devices.

An implant according to implementation of the invention includes anchors deployable via a 0° profile deployment method. The anchors may be deployable generally orthogonally to a plane of insertion of the implant. The anchors may be deployable within 10° of orthogonal to a plane of insertion of the implant. The anchors may each include a pair of blades extending generally orthogonally away from a base.

The implant may include a flexible beam adapted to be flexibly displaced from a resting position by placement of one of the anchors within the implant, and wherein when the anchor is deployed, the flexible beam returns to the resting position and prevents the anchor from leaving its deployed position. The implant may include two anchors, one deployable through a cranial surface of the implant and one deployable through a caudal surface of the implant. The implant may include four flexible beams, two flexible beams per anchor serving to prevent that anchor from leaving its deployed position.

The anchors may be deployable by inserting a flat blade between the anchors and by twisting the flat blade to force the anchors apart.

The implant may include a body formed of a biocompatible material, the body having a stiffness of between 400 megapascals (MPa) and 1,200 MPa, and the body having a plurality of pores having an average size of between 150 microns and 600 microns. The implant body may have a coil spring construction. The implant body may have a nested coil spring construction. The body may include a plurality of overlapping coil packs.

The implant may further include an inserter-engagement opening formed in a body of the implant and adapted to be engaged by an inserter during implantation of the implant and an anchor cavity housing the anchors. The anchor cavity may contain two opposed anchors, a first anchor adapted to extend in a cranial direction through one or more slots in a cranial surface of the implant, and a second anchor adapted to extend in a caudal direction through one or more slots in a caudal surface of the implant.

According to further implementation of the invention, an implant includes a body adapted to be inserted into an interbody space between two vertebral bodies of a human spine, the body including a cranial surface adapted to rest against one of the vertebral bodies and a caudal surface adapted to rest against the other of the vertebral bodies. The implant also includes an inserter-engagement opening formed in the body and an anchor cavity with a pair of two-bladed anchors disposed therein. The anchors are adapted to be deployable through slots in the cranial surface and in the caudal surface to engage with the vertebral bodies to fix the implant in the interbody space.

The anchors may each have a pair of blades extending generally orthogonally away from a base. The body may include four flexible beams serving to engage the anchors in a fully-deployed position such that the anchors are prevented from leaving the fully-deployed position. The anchors may be deployable by inserting a flat blade between the anchors and by twisting the flat blade to force the anchors apart. The flat blade may be inserted between the anchors and twisted while remaining entirely within an anterior axis of the implant. The inserter-engagement opening may be formed by adjacent coil packs sweeping into each other to form a detent with no solid external geometry that would alter a stiffness of the body. The detent may form a void adapted to engage tabs of an inserter device.

BRIEF DESCRIPTION OF THE SEVERAL VIEWS OF THE DRAWINGS

The objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described and explained with additional specificity and detail through the use of the accompanying drawings in which:

DETAILED DESCRIPTION OF THE INVENTION

Figure 1:
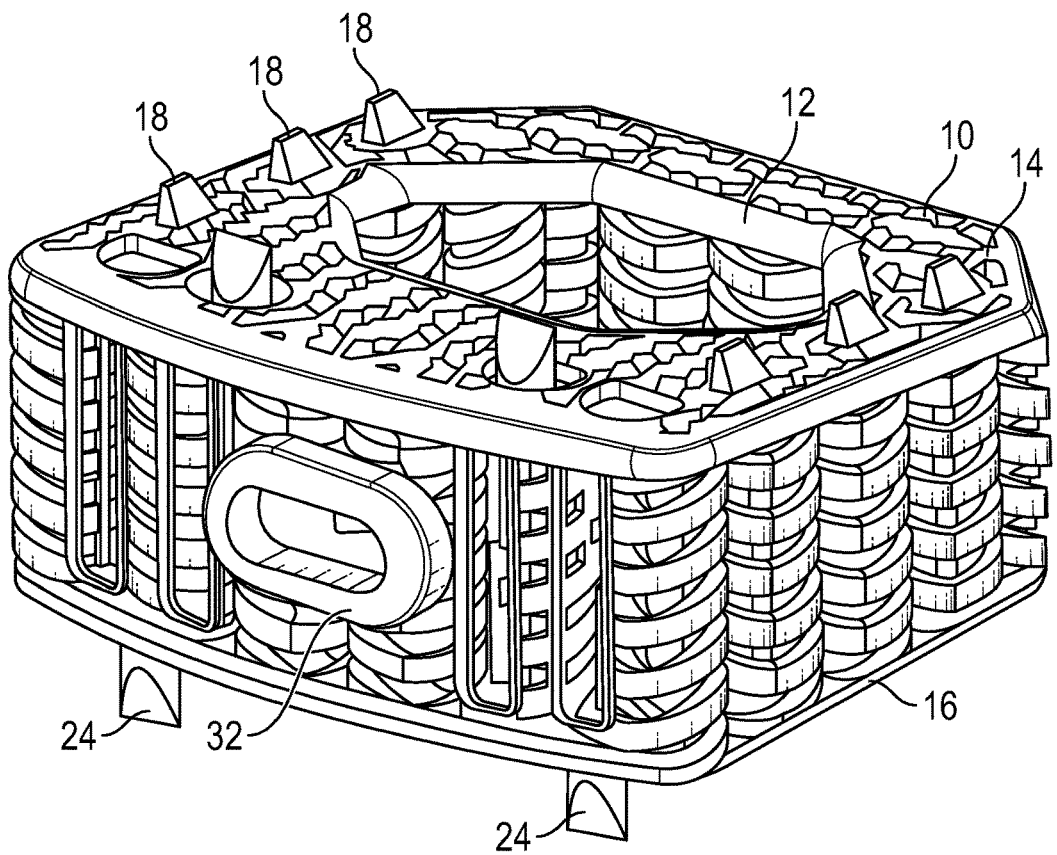
FIG. 1 shows a perspective view of one embodiment of an implant with deployable spikes in a deployed position.

A description of embodiments of the present invention will now be given with reference to the Figures. It is expected that the present invention may take many other forms and shapes, hence the following disclosure is intended to be illustrative and not limiting, and the scope of the invention should be determined by reference to the appended claims.

Embodiments of the invention provide improved fixation or stabilization of implants via one or more deployable spikes or anchors. The deployable spikes or anchors may be present in the implant in a nested, collapsed, or retracted position while the implant is inserted into the human body, and may then be deployed (e.g., into adjacent bone) after the implant is in place, thereby fixing the implant's location against unwanted movement. Such fixation or stabilization of the implant may reduce patients' pain, may improve overall short-term and long-term stability of the implant, and may improve osteo-integration into the implant.

The one or more deployable spikes or anchors of embodiments of the implant differ from traditional fixation systems in several regards. First, the deployable spikes or anchors are contained within the implant during the implant insertion procedure, and there is no need to later add a separate fixation device such as a screw or other anchor, and there is therefore no need for tools or implements that can secure and manipulate such a separate fixation device as it is brought to and added to the implant in-situ. Additionally, the deployable spikes or anchors move largely perpendicular to a general plane of symmetry of the implant, and therefore move into and anchor the implant in the adjacent bone in a direction generally orthogonal to an insertion direction taken by the implant during insertion. Accordingly, deployment of the deployable spikes or anchors better secures the implant against unwanted motion than do traditional anchoring devices that are inserted at angles other than generally orthogonal. Furthermore, the deployable spikes or anchors may be deployed using a simple manipulation of an anchor-deployment tool from a direct-anterior position after the implant is placed. This simple manipulation step minimizes the steps necessary for anchoring, minimizes forces applied to the implant after implant placement, and makes for extremely easy implant fixation or stabilization. Manipulation of the anchor-deployment tool can occur while an implant-insertion tool remains engaged with the implant, ensuring that proper implant placement is maintained while the deployable spikes or anchors are deployed.

An additional difference of the deployable spikes or anchors of the implant is that the deployable spikes or anchors may be returned to the nested, collapsed, or retracted position in the event a revision surgery becomes necessary. Accordingly, removal of the implant becomes much easier than with traditional implant fixation systems, as traditional fixation systems may require significant destruction of surrounding bony structures to obtain removal of the implant with its traditional fixation devices.

Embodiments of the fixation system may be used with a variety of implants, such as spinal interbody implants at any applicable level of the spine. While embodiments of the fixation system are intended for use with implants having a correct pore size and stiffness/flexibility as disclosed in U.S. patent application Ser. No. 15/372,290, filed Dec. 7, 2106, incorporated herein by reference for all it discloses, so as to achieve all the benefits of such implants as discussed in that application, embodiments of the fixation system may be used with spinal implants of other pore sizes or stiffnesses. Accordingly, while many of the exemplary embodiments discussed herein and illustrated in the Figures incorporate the pore size and stiffness features discussed in that prior application, one exemplary embodiment, the embodiment illustrated in FIGS. 10-13, does not incorporate those pore size and stiffness teachings to illustrate that embodiments of the fixation system may be utilized with implants of any stiffness or porosity. Accordingly, though not specifically illustrated in the Figures, it is envisioned that embodiments of fixation systems similar to those discussed herein may be used with implants having stiffnesses and porosities greater than or less than those discussed in the referenced prior application, solid implants without pores, implants having porosity and/or stiffness similar to those discussed in the referenced prior application but achieved through other means, and the like.

Figure 3:
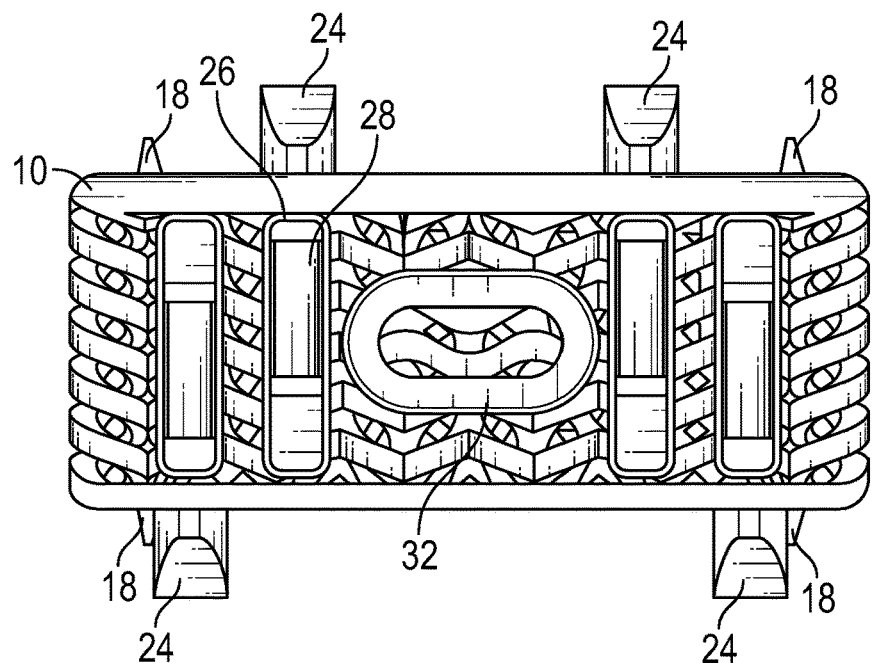
FIG. 3 shows an anterior side view of the embodiment of an implant of FIG. 1 with the deployable spikes in the deployed position.
Figure 4:
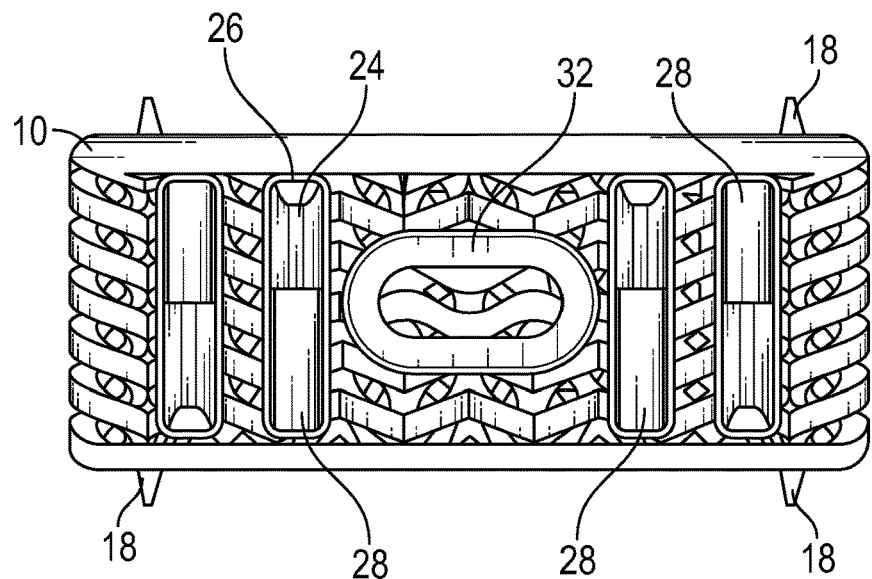
FIG. 4 shows an anterior side view of the embodiment of an implant of FIG. 1 with the deployable spikes in a nested, collapsed, or retracted position.
Figure 5:
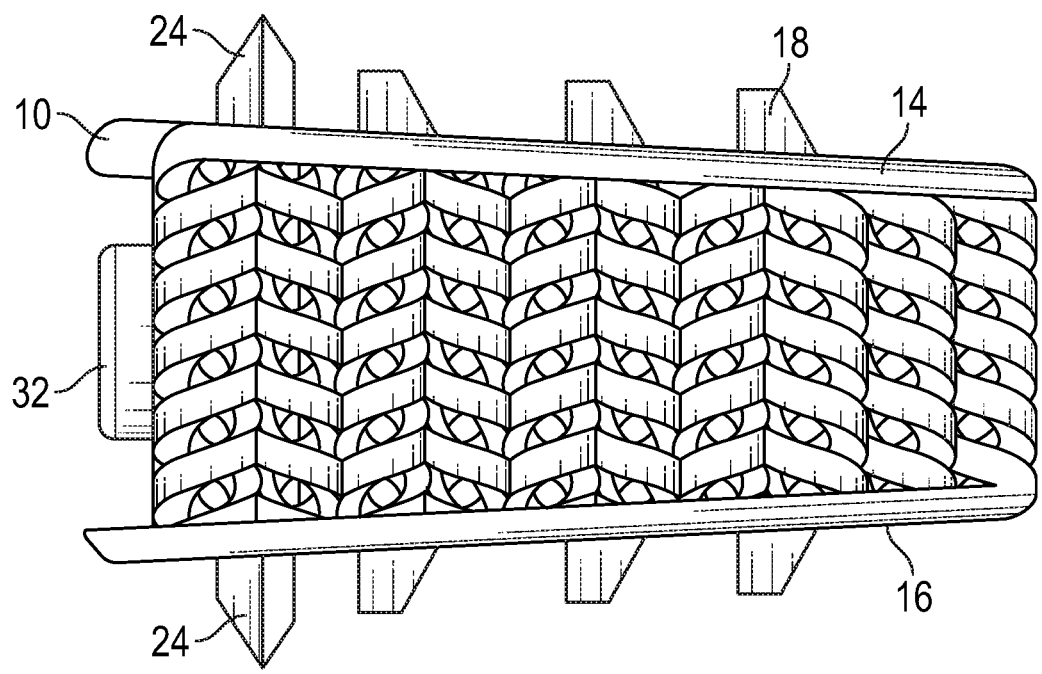
FIG. 5 shows a lateral side view of the embodiment of an implant of FIG. 1 with the deployable spikes in the deployed position.
Figure 6:
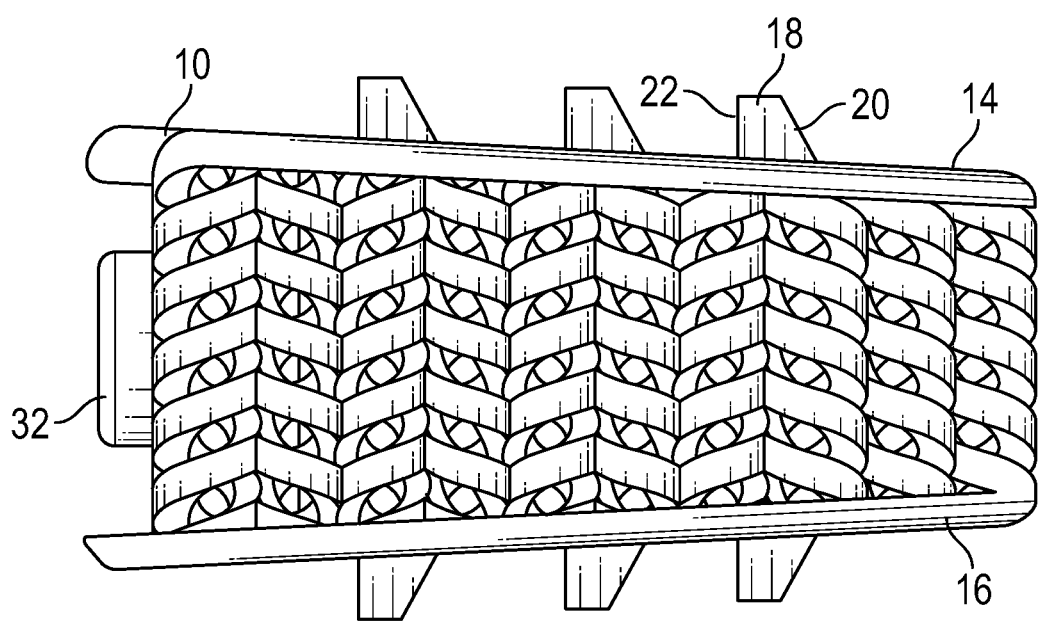
FIG. 6 shows a lateral side view of the embodiment of an implant of FIG. 1 with the deployable spikes in a nested, collapsed, or retracted position.
Figure 7:
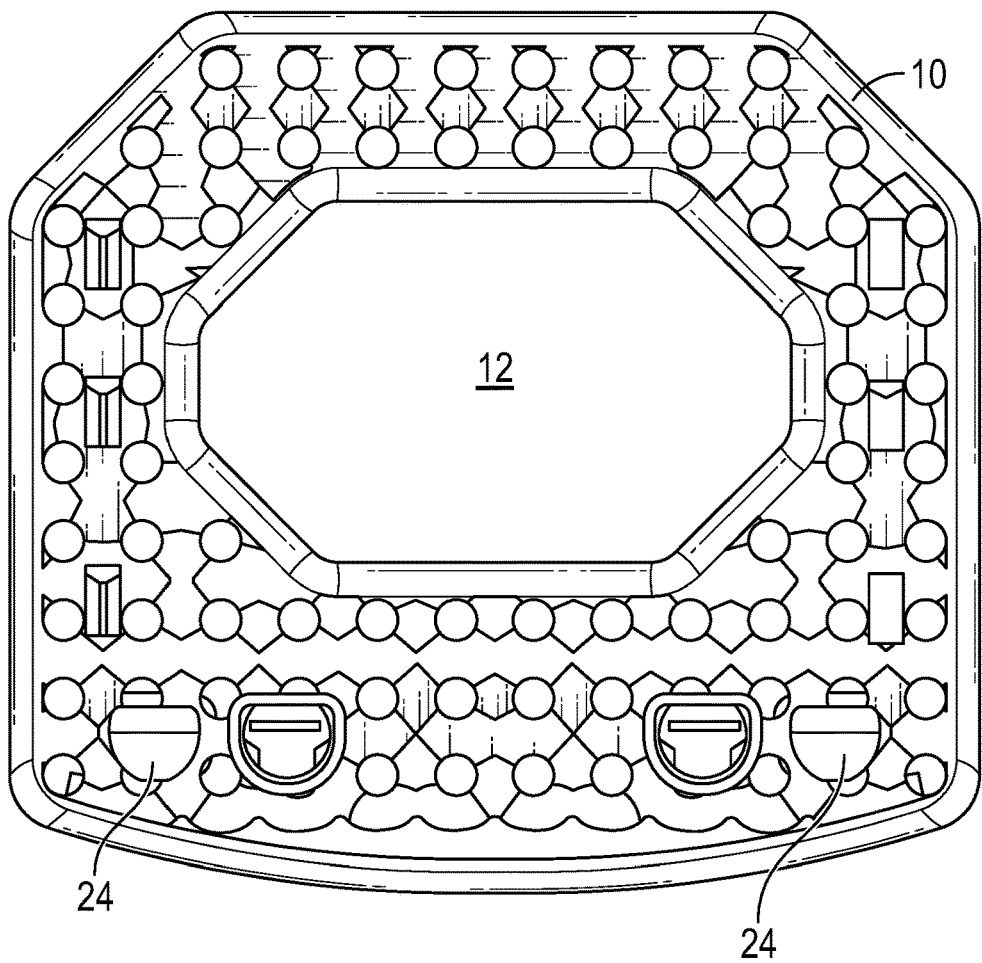
FIG. 7 shows a bottom view of the embodiment of an implant of FIG. 1.

FIGS. 1-8 illustrate one exemplary embodiment of an implant 10 intended for use in a total disc replacement procedure. The implant 10 is generally formed in accordance with the porosity and stiffness teachings of the referenced prior application, and includes a central window 12 adapted to receive a graft material such as morcellized bone and the like, as is known in the art. The implant 10 includes a cranial surface 14 adapted to contact a caudal surface of a vertebral body immediately to the cranial side of the implant 10 and a caudal surface 16 adapted to contact a cranial surface of a vertebral body immediately to the caudal side of the implant 10 once the implant 10 is implanted, e.g. via an ALIF (anterior lumbar interbody fusion) procedure. Each of the cranial surface 14 and the caudal surface 16 include one or more teeth 18 protruding therefrom. The one or more teeth 18 may be shaped (as best illustrated in FIGS. 5 and 6) to permit entry of the implant 10 into the interbody space between vertebral bodies, but to generally resist withdrawal of the implant 10 from the interbody space. By way of example, as illustrated in FIG. 6, each tooth 18 may have a leading edge 20 disposed at an acute or swept-back angle to the underlying respective cranial surface 14 or caudal surface 16, and a trailing edge 22 disposed generally orthogonally to the underlying cranial surface 14 or caudal surface 16.

The specific shape and number of the teeth 18 illustrated in FIGS. 1-8 are merely provided as one example, and it should be understood that the number, shape, and size of the teeth 18 may be varied as desired to achieve a desired ease of implantation and resistance to withdrawal of the implant 10. While the teeth 18 may provide some fixation to the implant 10 upon implantation, the teeth 18 are assisted in the fixation function by one or more spikes 24 that are configured to movingly extend from the cranial surface 14 and/or the caudal surface 16 in a direction generally orthogonal to a plane of insertion of the implant 10. In some embodiments, the one or more spikes 24 may move and extend orthogonally or generally orthogonally from a plane of insertion of the implant 10 (in the example of the implant of FIGS. 1-8, the plane of insertion is the plane bisecting the implant and extending orthogonally from the page along a horizontal line in any of FIGS. 3-6). In other embodiments, the one or more spikes 24 may move and extend orthogonally or generally orthogonally from the cranial surface 16 and/or the caudal surface 18.

In some embodiments, the generally orthogonal movement and extension of the one or more spikes 24 embraces a movement and extension of between 0° and 2° from orthogonal. In other embodiments, the generally orthogonal movement and extension of the one or more spikes 24 embraces a movement and extension of between 0° and 4° from orthogonal. In other embodiments, the generally orthogonal movement and extension of the one or more spikes 24 embraces a movement and extension of between 0° and 6° from orthogonal. In other embodiments, the generally orthogonal movement and extension of the one or more spikes 24 embraces a movement and extension of between 0° and 8° from orthogonal. In other embodiments, the generally orthogonal movement and extension of the one or more spikes 24 embraces a movement and extension of between 0° and 10° from orthogonal. In other embodiments, the generally orthogonal movement and extension of the one or more spikes 24 embraces a movement and extension of between 0° and 12° from orthogonal. In other embodiments, the generally orthogonal movement and extension of the one or more spikes 24 embraces a movement and extension of between 0° and 14° from orthogonal. In other embodiments, the generally orthogonal movement and extension of the one or more spikes 24 embraces a movement and extension of between 0° and 16° from orthogonal. In other embodiments, the generally orthogonal movement and extension of the one or more spikes 24 embraces a movement and extension of between 0° and 18° from orthogonal. In other embodiments, the generally orthogonal movement and extension of the one or more spikes 24 embraces a movement and extension of between 0° and 20° from orthogonal.

In some embodiments where more than one spike 24 is present, at least one spike 24 extends from the cranial surface 14 and at least one spike extends from the caudal surface 16. In some such embodiments, the spike 24 extending from the cranial surface 14 moves along an axis of movement that is generally parallel to an axis of movement of the spike 24 extending from the caudal surface 16. In other such embodiments, the spike 24 extending from the cranial surface 14 moves along an axis of movement that is inclined generally opposite an angle of inclination of an axis of movement of the spike 24 extending from the caudal surface 16 relative to the plane of insertion.

In some embodiments where multiple spikes 24 are present, one or more spikes 24 may move independently of one or more other spikes 24. In other embodiments where multiple spikes are present, groups of two or more spikes may move together, such as by being unitarily formed. As a specific example of such, any spikes 24 adapted to extend from the cranial surface 14 may be unitarily formed but separate from any spikes 24 adapted to extend from the caudal surface 16, which may together be unitarily formed. In this way, the cranial spikes 24 may move together in a motion opposite to the motion of the caudal spikes 24, which also move together.

Figure 2:
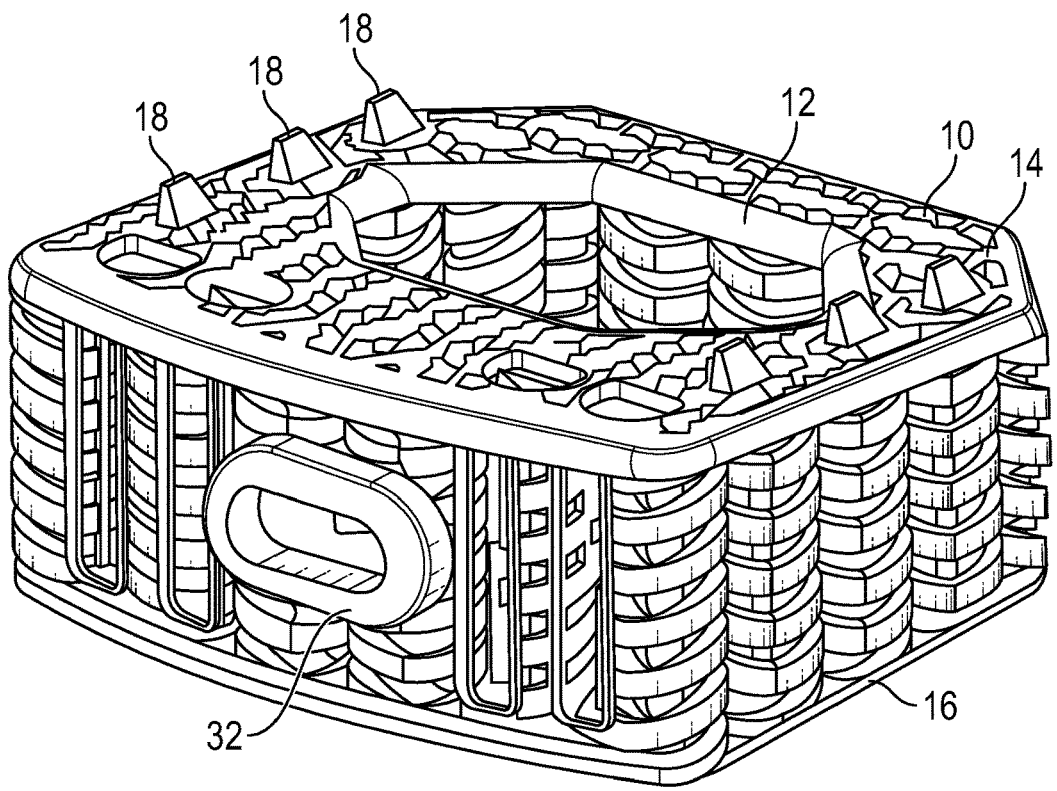
FIG. 2 shows a perspective view of the embodiment of an implant of FIG. 1 with the deployable spikes in a nested, collapsed, or retracted position.

When the implant 10 is initially provided, and then during insertion of the implant 10 into the interbody space, the one or more spikes 24 may be in a nested, retracted, or collapsed position, as illustrated in FIGS. 2, 4, and 6. Once the implant 10 has been placed in its final position within the interbody space, the one or more spikes 24 may be manipulated through their (generally linear) range of motion to a deployed position at which the one or more spikes 24 extend from the respective surface (the cranial surface 14 or the caudal surface 16). Because the cranial surface 14 and the caudal surface 16 are generally adapted to rest against the bone of the respective vertebral bodies, when the one or more spikes 24 move to extend from the implant surface(s), the spikes will generally contact and then penetrate the bone of the vertebral body or bodies. This penetration of the one or more spikes 24 into the adjoining bone will further fix the implant 10 in place. The one or more spikes 24 may have a sharp tip to facilitate penetration of the one or more spikes 24 into the bone, as illustrated in the Figures.

When the one or more spikes 24 is in the nested, retracted, or collapsed position, the tips of the one or more spikes 24 may lie entirely within the implant (e.g., flush with or interior of the implant 10 to the respective cranial surface 14 or caudal surface 16). Alternatively, the one or more spikes 24, in the nested, retracted, or collapsed position, may extend slightly beyond the respective surface, such as an amount no greater than the distance above the surface to which the teeth 18 extend. When the one or more spikes 24 protrude a small amount in the nested, retracted, or collapsed position, the small protrusion may not provide significant resistance to insertion of the implant 10, but may allow for greater travel and penetration of the one or more spikes 24 into the surrounding bone.

In some embodiments, the movement of the one or more spikes 24 to the fully deployed or fully extended position may be a one-time event. In other words, some feature of the implant 10 may lock the one or more spikes 24 in such embodiments against unwanted collapsing of the one or more spikes 24, such that once the one or more spikes 24 is fully deployed or extended, it is prevented against collapse by the anti-collapse feature. In some such embodiments, the spike may be permitted to collapse again upon application of a force sufficient to destroy the anti-collapse feature (such force being one that would not be experienced by the implant 10 except upon intentional action taken to ready the implant 10 for removal), but such action might render the implant 10 incapable of again locking the one or more spikes 24 in the fully deployed or fully extended position. In other embodiments, the movement of the one or more spikes 24 may be reversible, such as upon intentional manipulation of a locking feature of the implant 10.

Figure 8:
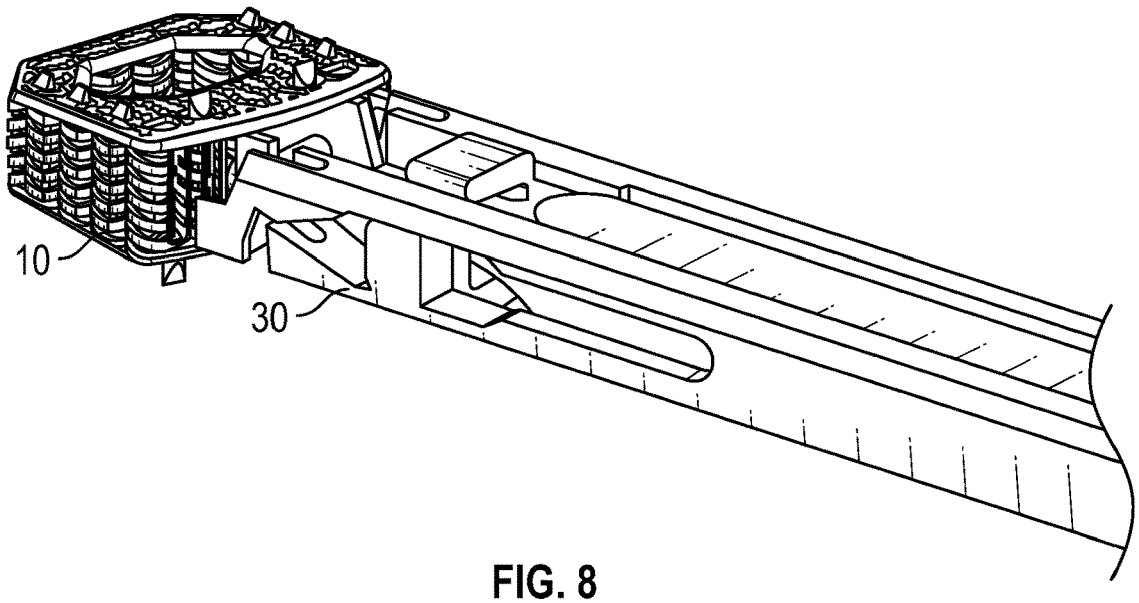
FIG. 8 shows a perspective view of the embodiment of an implant of FIG. 1 secured on an end of an inserter device, with the deployable spikes in a deployed position.

FIGS. 3 and 4 show an anterior view of the implant 10 and show that the anterior surface of the implant is provided with spike access channels 26. The spike access channels 26 may provide access to a lip or other internal portion 28 of the one or more spikes 24 such that an outward-directed force may be applied to each of the one or more spikes 24 by a spike-deployment tool 30, as illustrated in FIG. 8. The spike-deployment tool 30 may engage the lip or other internal portion 28 of the one or more spikes 24 and may provide a deploying force to each of the one or more spikes 24 either serially or collectively upon manipulation of the spike-deployment tool 30.

The implant 10 also includes an inserter-engagement opening 32 adapted to engage an inserter or insertion tool adapted to secure the implant 10 thereon and to facilitate manipulation of the implant 10 during insertion of the implant 10 into the interbody space. The inserter or insertion tool may engage with and secure the implant 10 at the inserter-engagement opening 32 and may be locked to the inserter or insertion tool until final placement has been achieved. In some embodiments, the spike-deployment tool 30 may be integrated with the inserter or insertion tool as a single tool. In other embodiments, the inserter or insertion tool may be removed from the implant before the spike-deployment tool 30 is engaged with the implant 10 and manipulated to deploy the one or more spikes 24. As another option, the inserter or insertion tool may be separate from the spike-deployment tool 30, but may remain engaged with the implant 10 while the spike-deployment tool 30 is engaged with the implant 10 and manipulated to deploy the one or more spikes 24. By remaining engaged with the implant 10, the inserter or insertion tool may serve to prevent unwanted movement of the implant 10 while the spike-deployment tool 30 is manipulated to deploy the one or more spikes 24.

As may be seen in and appreciated by FIG. 8, the spike-deployment tool 30 (and the inserter or insertion tool) may be adapted to extend from the implant 10 essentially in a directly anterior direction. Manipulation of the spike-deployment tool 30 to deploy the one or more spikes 24 may be achieved by mechanical linkages such that the spike-deployment tool 30 remains in the anterior direction from the implant 10. Accordingly, it will be appreciated that there is no requirement of accessing the implant 10 from an oblique angle to achieve deployment of the one or more spikes 24, despite the fact that the one or more spikes 24 deploy in a generally orthogonal direction from the plane of insertion of the implant 10, which angle of fixation element deployment is not achievable via traditional spinal implants. The deployment of the one or more spikes 24 occurs entirely in situ, after insertion of the implant 10 into the interbody space.

As may be appreciated from the illustrated embodiment of FIGS. 1-8, the implant 10 may have a total of four spikes 24. Two spikes may extend from the cranial surface 14 and two spikes may extend from the caudal surface 16. While the embodiment of FIGS. 1-8 includes four spikes, it should be appreciated that other embodiments may have more or fewer spikes 24. Additionally, the number and size of the spikes 24 may vary, such as between an implant 10 intended for cranial use as opposed to an implant 10 intended for lumbar use. Accordingly, the specific dimensions and features of the implant 10 shown in FIGS. 1-8 may be varied for a number of reasons.

Figure 9:
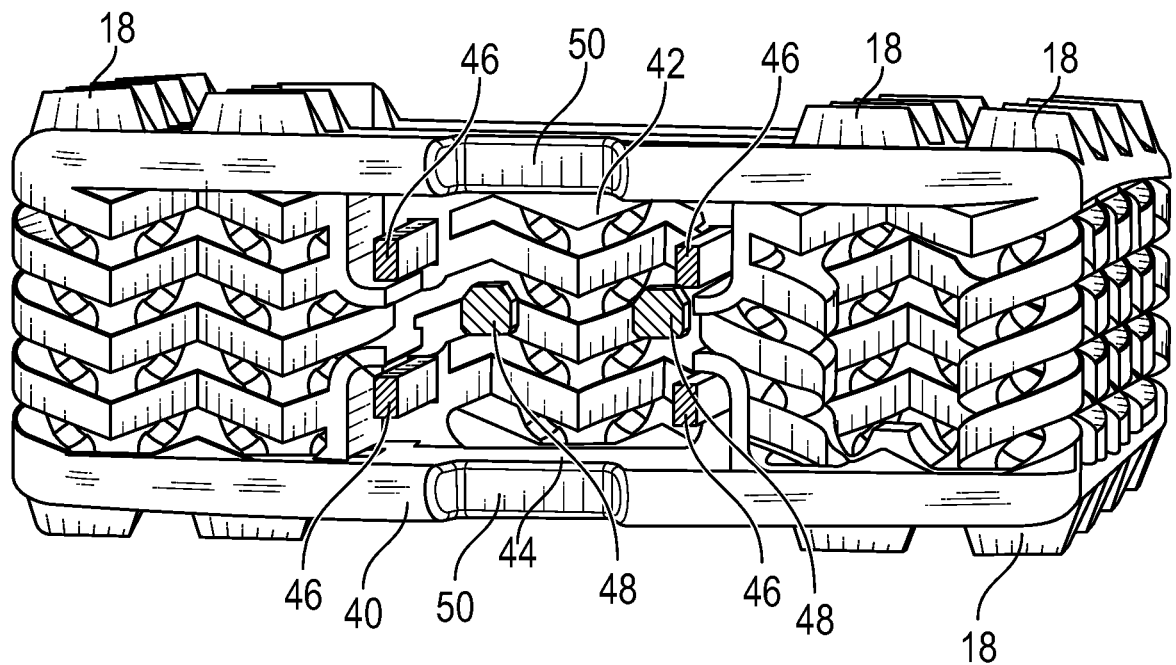
FIG. 9 shows a perspective view of an alternate embodiment of an implant, with deployable anchors absent to show features of an anchor recess.
Figure 22:
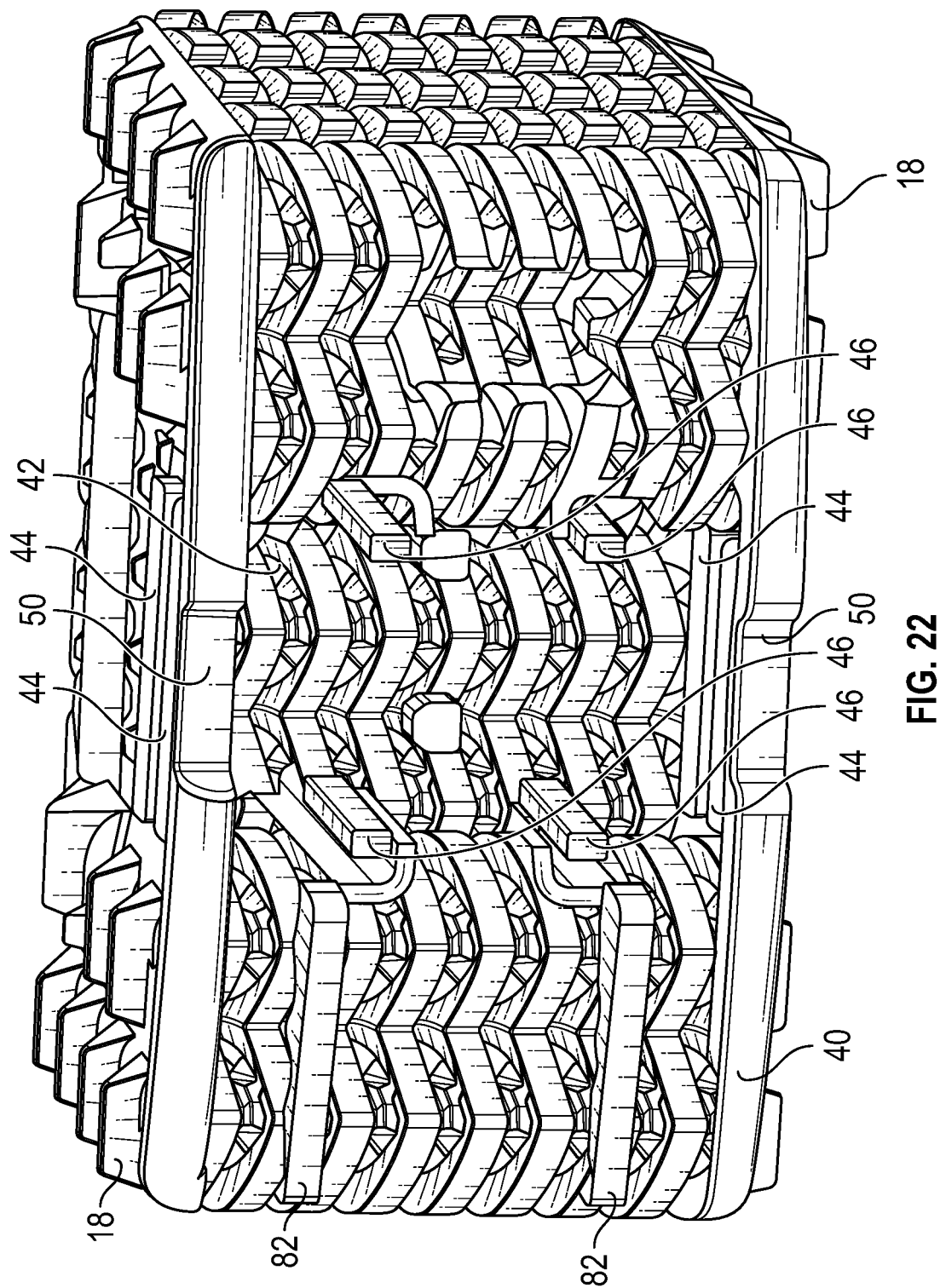
FIG. 22 shows a perspective view of an alternate embodiment of an implant with deployable anchors absent.

FIG. 9 shows an alternate embodiment of an implant 40. This implant 40 includes many features similar to the features discussed with respect to the implant 10 of FIGS. 1-8, but utilizes anchors (not shown in FIG. 9, but illustrated with respect to the embodiments shown in FIGS. 10-30). The implant 40 includes multiple rows of teeth 18 on each side of the cranial surface 14 and the caudal surface 16, illustrating how the teeth 18 may be varied between embodiments. In FIG. 22, the anchors are not shown so as to permit discussion of features of an anchor cavity 42 disposed centrally on the anterior surface of the implant 40.

The anchor cavity 42 communicates with the cranial surface 14 and with the caudal surface 16 via slots 44 that each permit passage of a vertical blade of an anchor therethrough to moveably extend into the bone as with the spikes 24 discussed previously. Within the anchor cavity 42 are flexible cantilever beams 46 or locking tabs. The beams 46 are displaced laterally when the anchors are present in the nested, collapsed, or retracted position. However, when the anchors are moved fully outwardly to engage and penetrate the bone of the vertebral bodies, the anchors no longer displace the beams 46 laterally, and the beams return to their native position, preventing the anchors from retracting again unless the beams 46 are manually displaced laterally again via an anchor retracting tool. In the event the beams 46 were to fail, a pair of raised lips 48 serves to prevent the anchors from migrating out of the implant. A medial notch 50 is present on each of the end plates of the implant 40, to permit a tool to engage the anchors in the event collapsing of the anchors is necessary.

The implant 40 includes the inserter-engagement opening 32, this time placed to the side of the anterior surface of the implant 40. The inserter-engagement opening 32 allows the inserter or insertion tool to engage and secure the implant 40, while an anchor-deployment tool engages the anchors in the anchor cavity 42 to deploy the anchors.

FIGS. 10-13 illustrate an alternate implant 60 having many of the features of the implant 40, and illustrating the engagement of anchors 62 with the anchor cavity and its features as discussed above. As may be seen in FIGS. 10-13, the anchors 62 rest in the anchor cavity 42 and are formed of two vertical blades 64 formed with or attached to a horizontal base 66. The horizontal base may be engaged to force the two anchors 62 apart, thereby forcing the sharp-tipped blades 66 into the bone by way of a simple flat-tip screwdriver type of anchor-deployment tool that causes the anchors 62 to deploy by a simple twisting motion.

Figure 10:
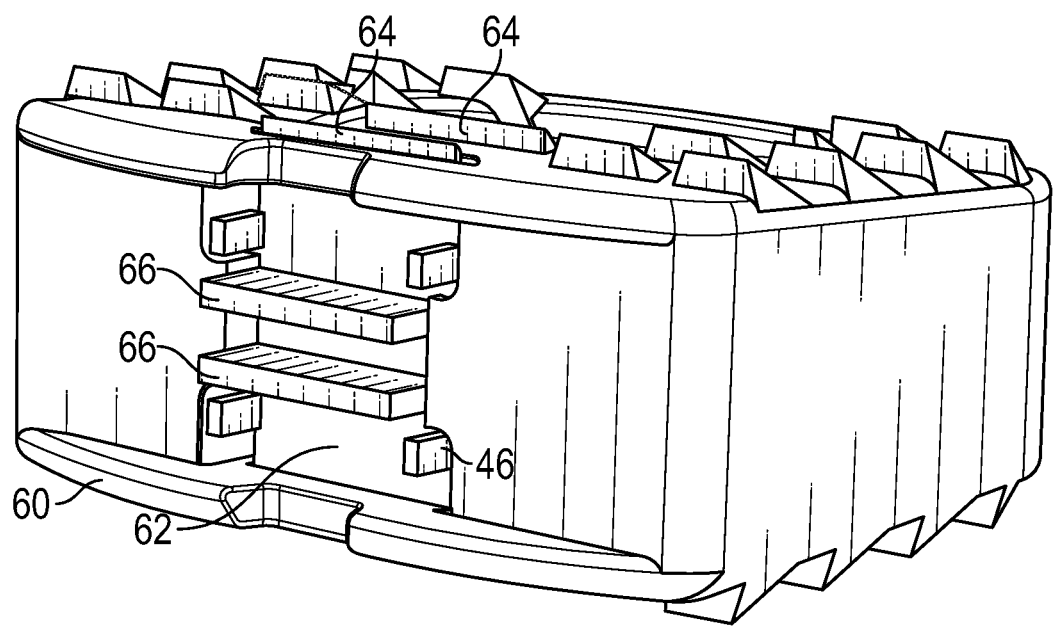
FIG. 10 shows a perspective view of an alternate embodiment of an implant with deployable anchors in a collapsed position.
Figure 11:
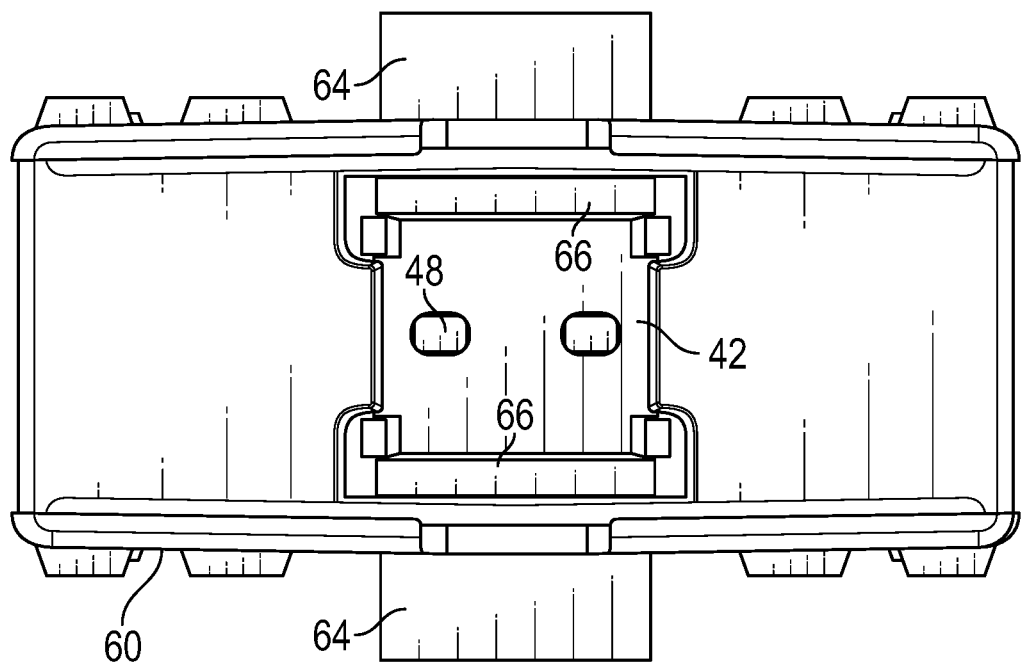
FIG. 11 shows an anterior side view of the embodiment of an implant of FIG. 10, with the deployable anchors in a deployed position.
Figure 12:
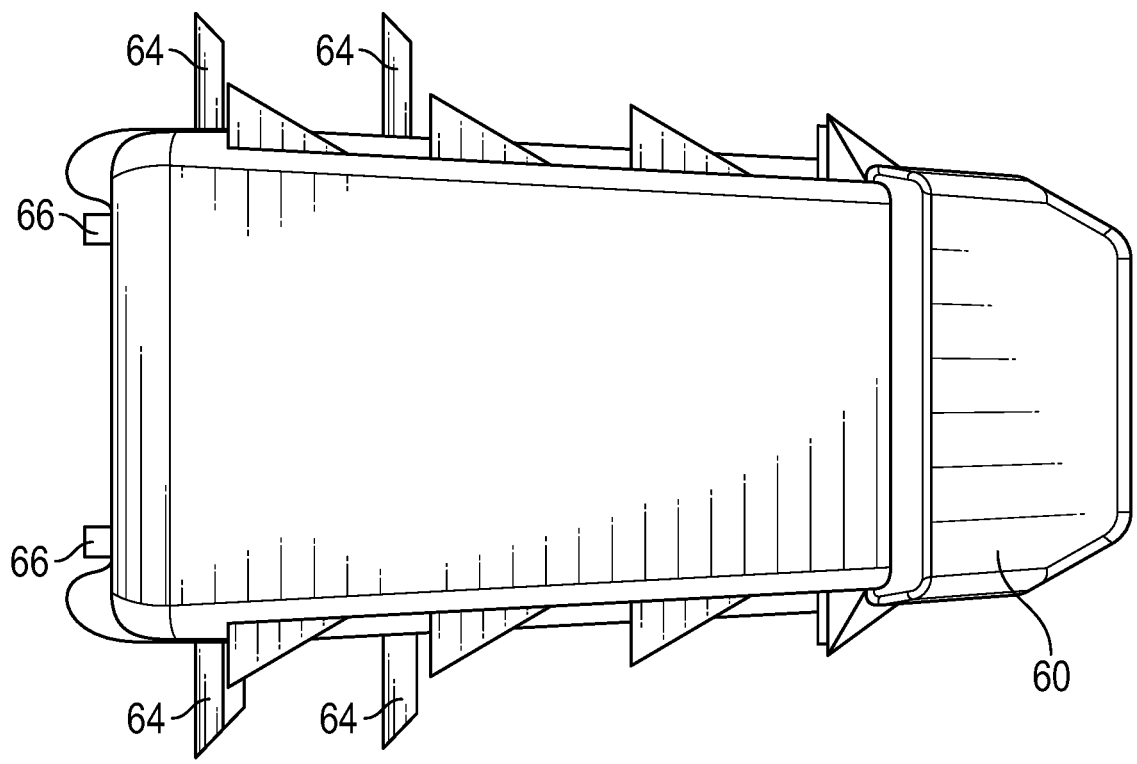
FIG. 12 shows a lateral side view of the embodiment of an implant of FIG. 10, with the deployable anchors in the deployed position.
Figure 13:
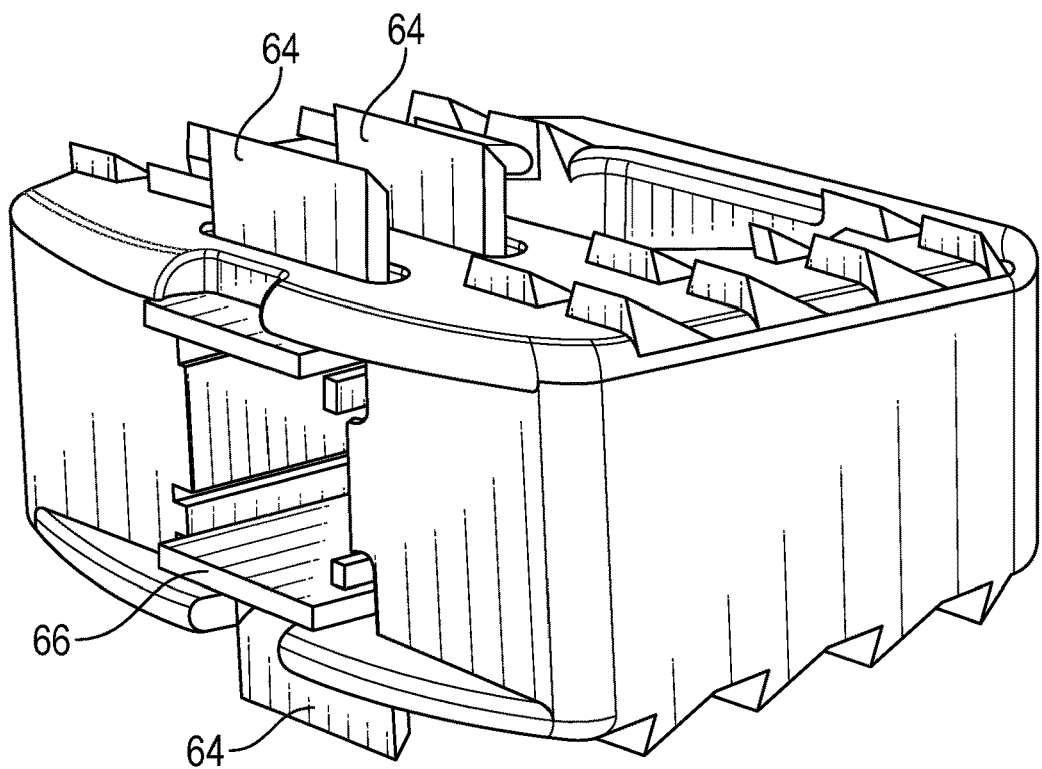
FIG. 13 shows a perspective view of the embodiment of an implant of FIG. 10, with the deployable anchors in the deployed position.
Figure 14:
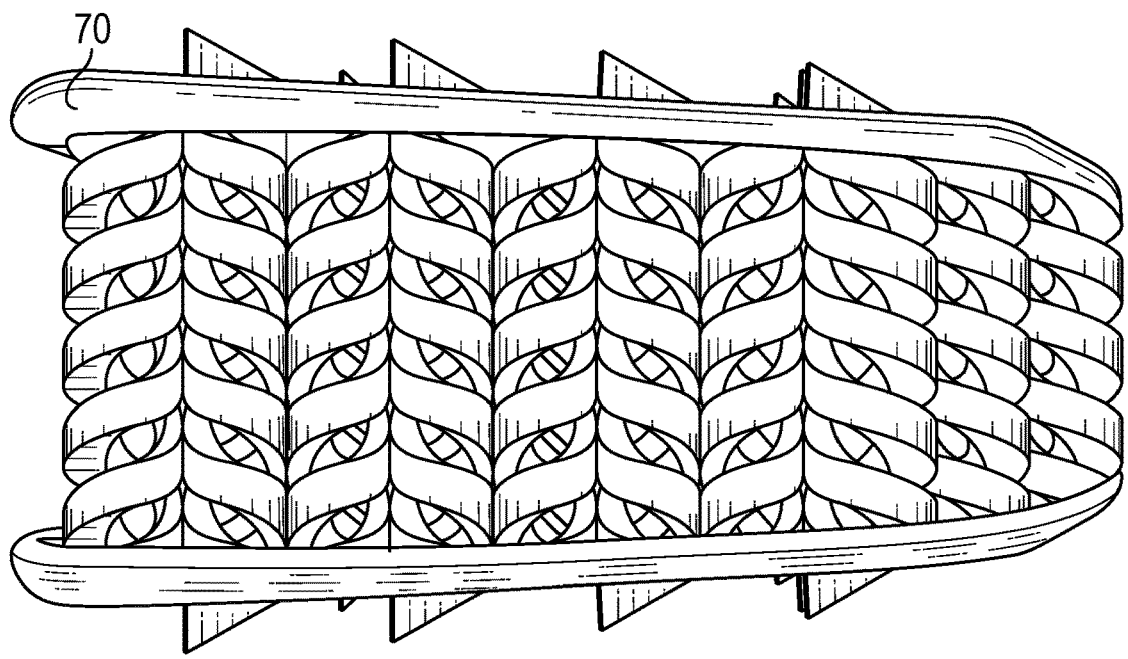
FIG. 14 shows a lateral side view of an alternate embodiment of an implant with deployable anchors in a collapsed position.

As illustrated in FIG. 10, the anchors 62 are collapsed during insertion of the implant 60, and the blades only minimally protrude from the cranial and caudal surfaces of the implant 60. After the implant 60 is placed, the anchor-deployment tool is inserted between the bases 66 of the anchors 62 and twisted to force the anchors 62 apart, causing the blades 64 to engage and penetrate the bone, securely fixing the implant 60 in place. If the implant 60 ever needs to be removed, a tool can engage the bases 66 at the medial notches 50, and the anchors 62 can be drawn together, either destroying the beams 46, or in conjunction with an action displacing the beams 46 laterally. Accordingly, removal can be easily achieved but is unlikely to occur unintentionally after implantation of the implant 60.

FIGS. 14-16 and 21 illustrate an alternate implant 70 having features of the implants discussed previously with respect to the other implant 10, implant 40, and implant 60. The implant 70 may have a roughened surface to further facilitate fixation of the implant 70 upon placement. The roughened surface may be achieved via an additive manufacturing (3-D printing) process used to manufacture the body of the implant 70. The implant 70 includes the porosity and stiffness features discussed in the prior related application discussed above.

Figure 17:
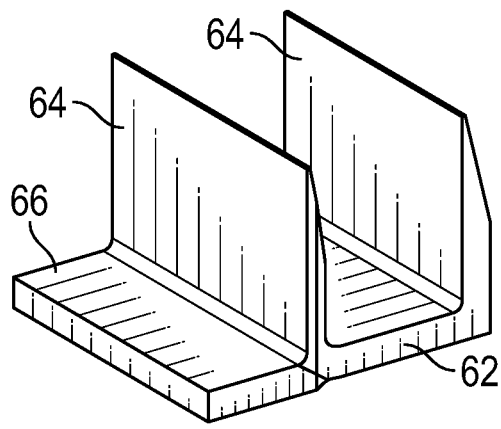
FIG. 17 shows a perspective view of an embodiment of a deployable anchor.
Figure 18:
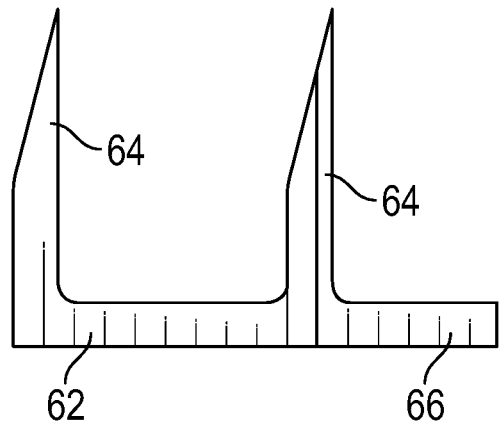
FIG. 18 shows a side view of the embodiment of the deployable anchor of FIG. 17.
Figure 19:
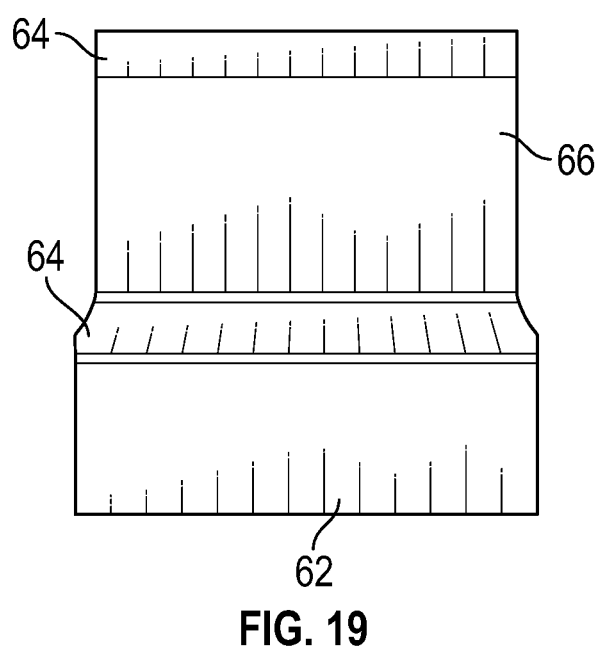
FIG. 19 shows a top view of the embodiment of the deployable anchor of FIG. 17.
Figure 20:
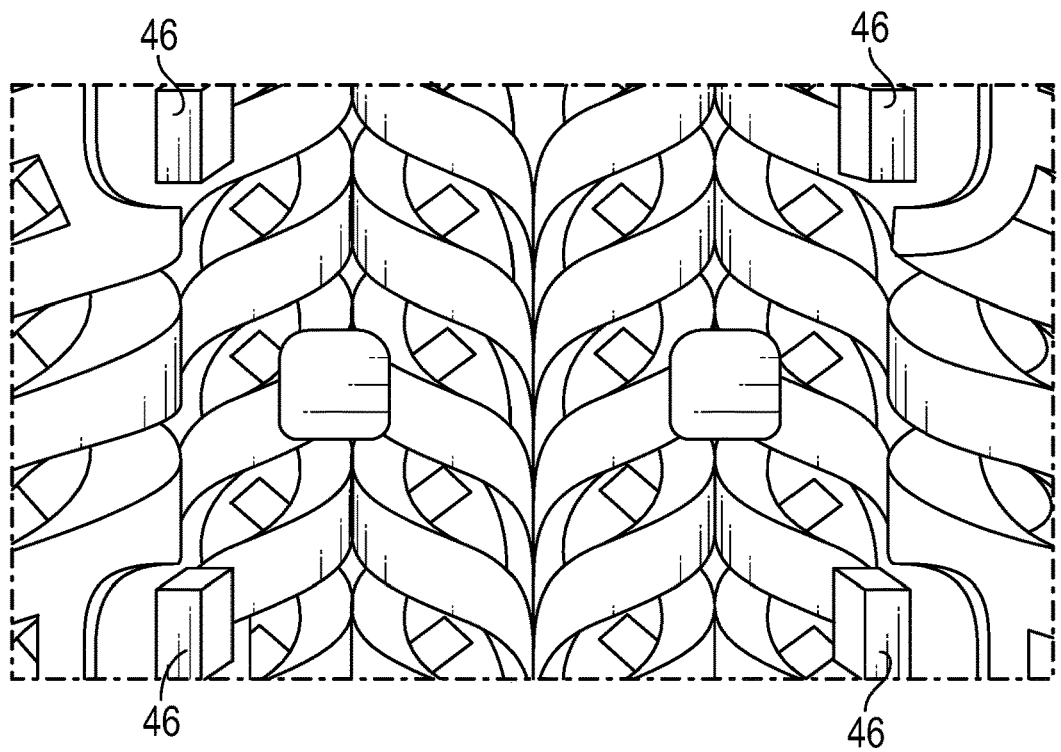
FIG. 20 shows an enlarged view of an anchor cavity of the embodiment of an implant of FIG. 15.
Figure 21:
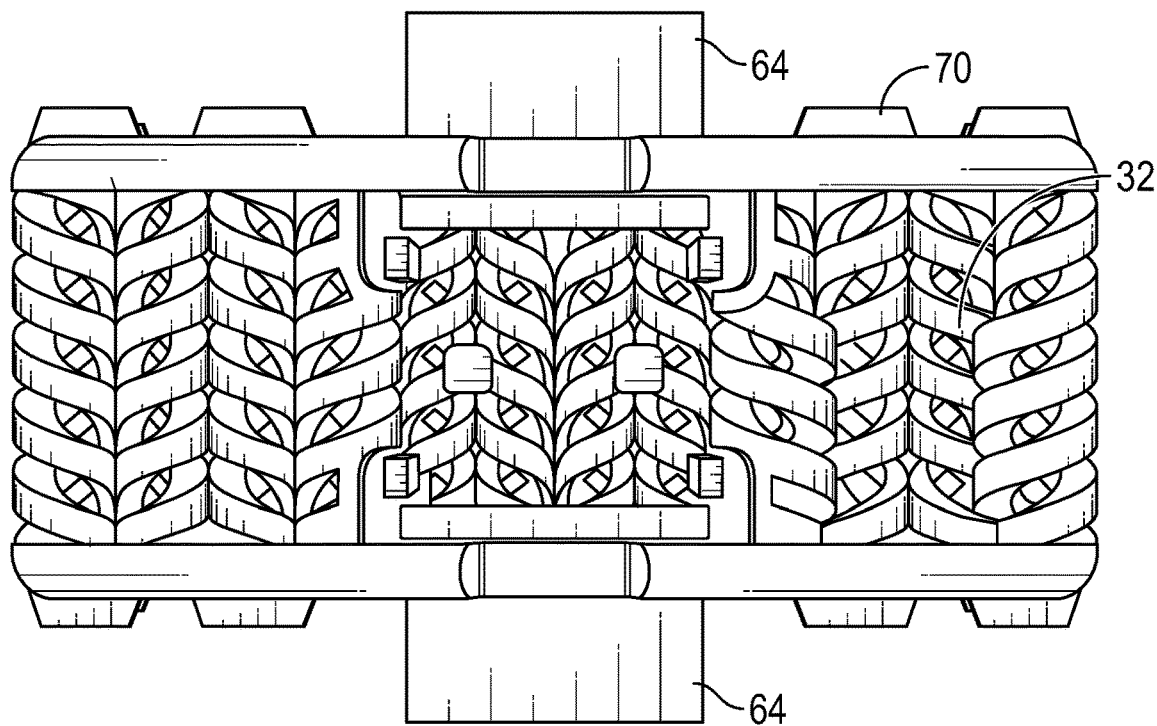
FIG. 21 shows an anterior side view of the embodiment of an implant of FIG. 15 with the deployable anchors in a deployed position.

FIGS. 17-19 illustrate an embodiment of the anchor 62 discussed above. The anchor 62 tapers in width to allow for ease of assembly and for interaction with the beams 46. The taper prevents the cantilevered beams from deflecting at the base of the tabs. FIG. 20 shows an enlarged view of one embodiment of the anchor cavity 42.

FIG. 22 illustrates an embodiment of an implant 80 that is larger in size and may be used in a larger interbody space. The implant 80 includes many of the features discussed with respect to the implant 40 of FIG. 9. The implant 80 may additionally include anti-rotation rims 82 that engage with a protuberance of the inserter or insertion tool to prevent rotation of the implant 80 during anchor deployment.

Figure 15:
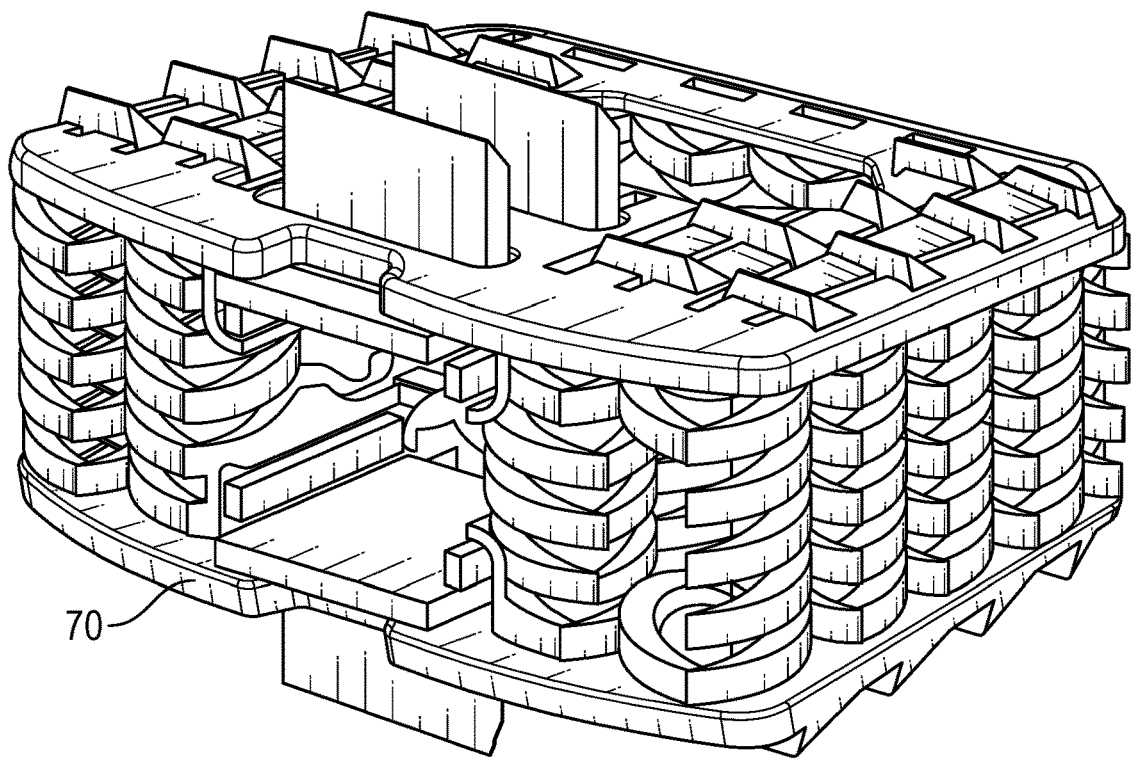
FIG. 15 shows a perspective view of the embodiment of an implant of FIG. 15 with the deployable anchors in a deployed position.
Figure 16:
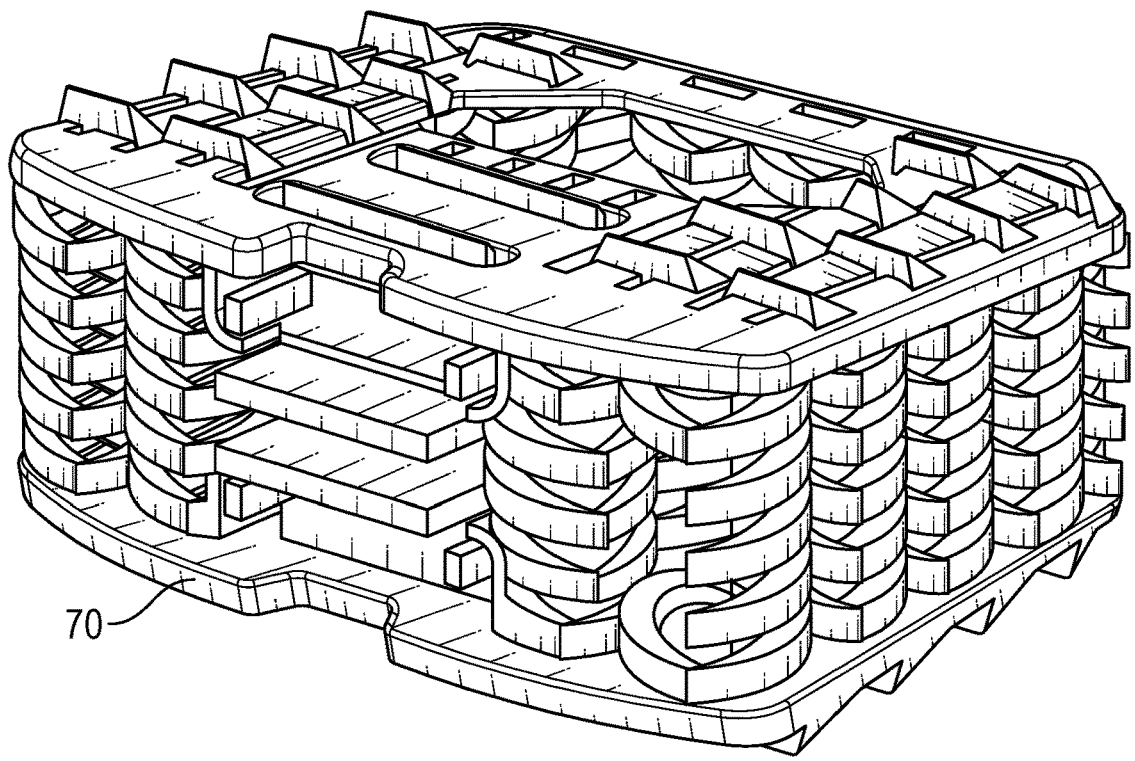
FIG. 16 shows a perspective view of the embodiment of an implant of FIG. 15 with the deployable anchors in the collapsed position.

FIGS. 25-30 illustrate an embodiment of an implant inserter 90 that is adapted to engage the inserter-engagement opening 32. The inserter-engagement opening 32 may be formed of adjacent coil packs (as disclosed in U.S. patent application Ser. No. 15/372,290 incorporated by reference herein) sweeping into each other to form a detent, as best illustrated in FIGS. 15 and 16. There are no external threads, rims, or solid geometry in this embodiment that would alter the stiffness profile of the implant 70. Rather, a void in the porous structure of the implant itself creates the inserter interface.

Figure 23:
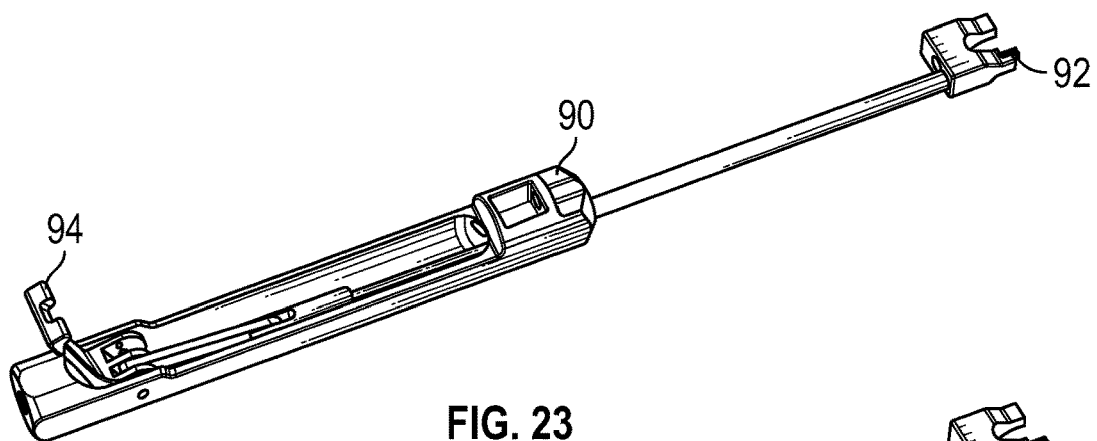
FIG. 23 shows a perspective view of an inserter tool.
Figure 24:
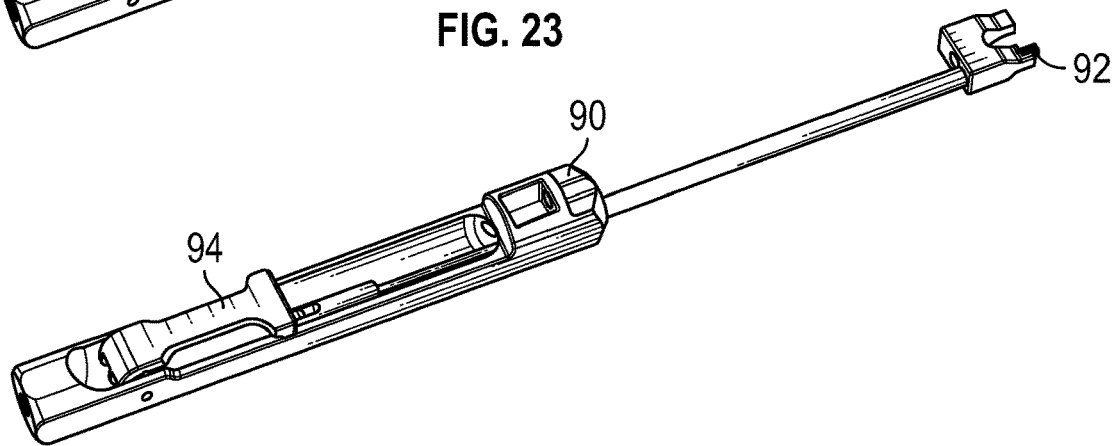
FIG. 24 shows a perspective view of the inserter tool of FIG. 23.
Figure 25:
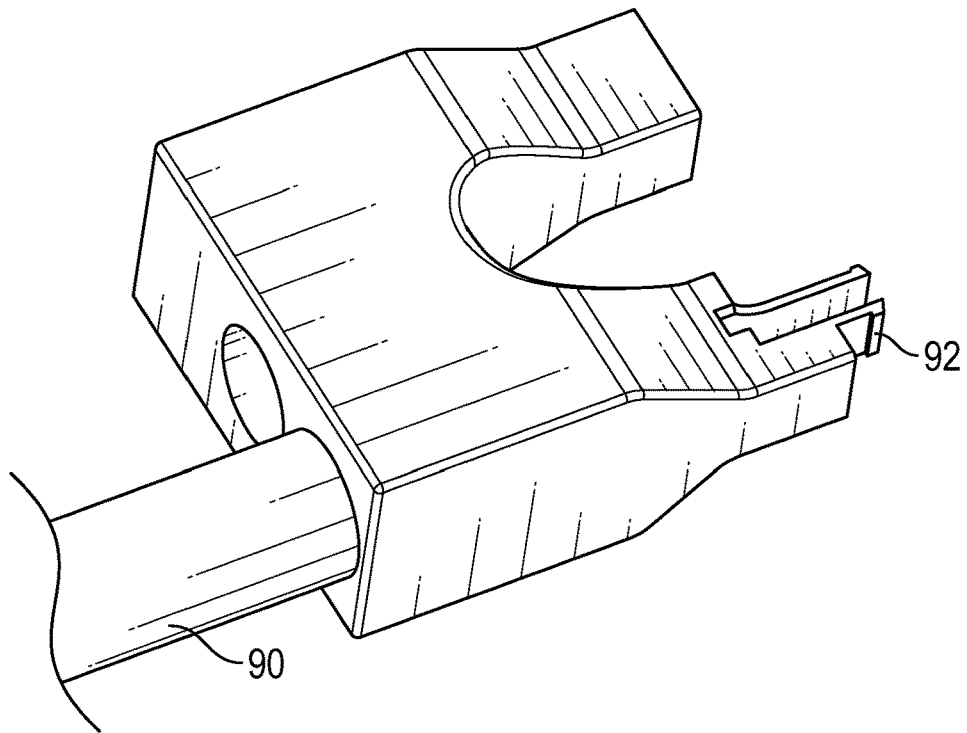
FIG. 25 shows a perspective view of an implant-engaging end of the inserter tool of FIG. 23.
Figure 26:
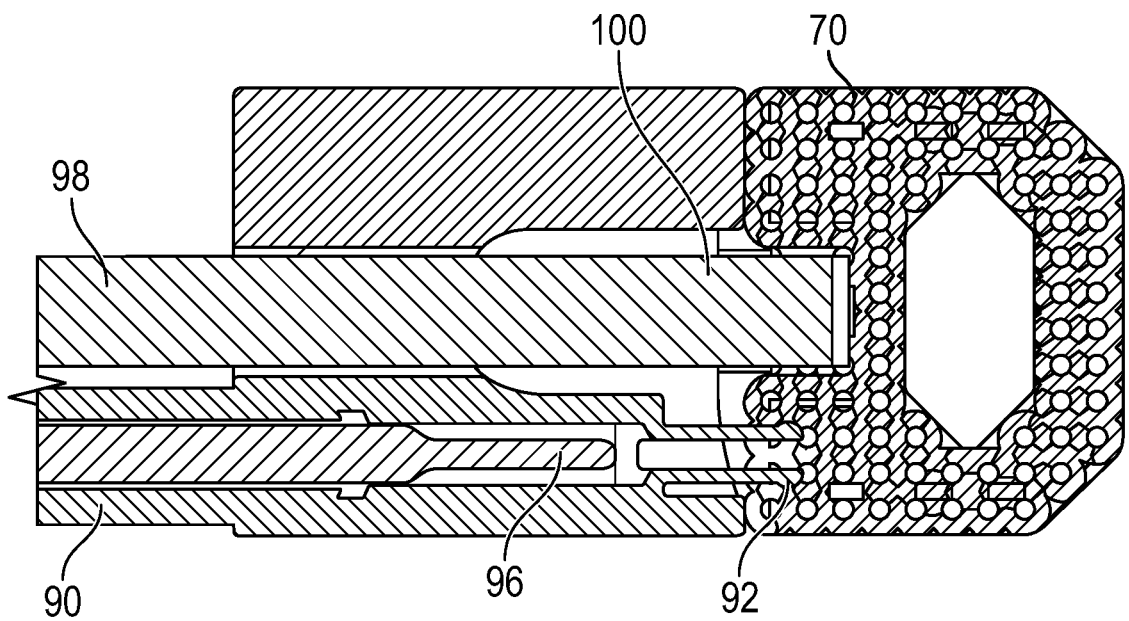
FIG. 26 shows a top plan view of an inserter tool and an anchor-deployment tool engaging with an embodiment of an implant.
Figure 27:
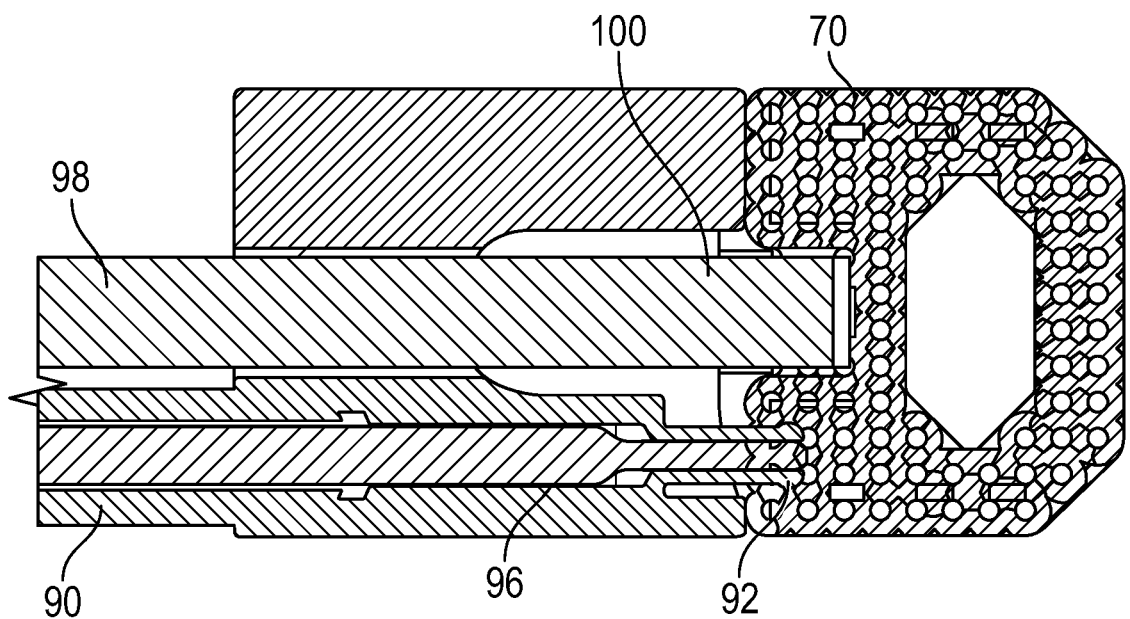
FIG. 27 shows a top plan view of the inserter tool and the anchor-deployment tool of FIG. 26 engaging with the embodiment of an implant of FIG. 26.
Figure 28:
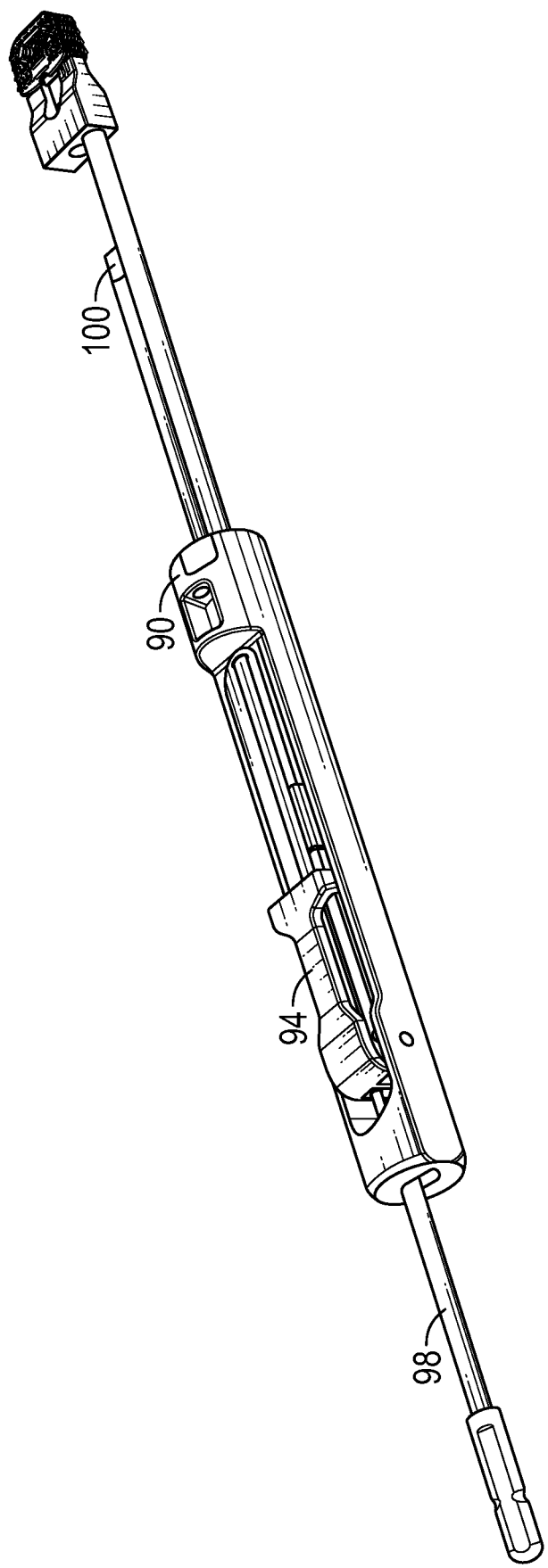
FIG. 28 shows a perspective view of an anchor-deployment tool engaging with an embodiment of an implant to deploy anchors of the implant while the implant is engaged with an inserter tool.

The distal end of the inserter 90 has flexible tabs 92 (FIG. 25) that snap into the implant inserter interface (with an operation lever 94 raised (FIGS. 23 and 26). Lowering the lever 94 pushes an expansion shaft 96 between the flexible tabs 92, expanding the tabs 92 sideways (FIGS. 24 and 27). The tabs 92 grab the internal surfaces of the implant while the expansion shaft 96 enables the tabs 92 to provide a stabilizing force to the inserter interface.

Figure 29:
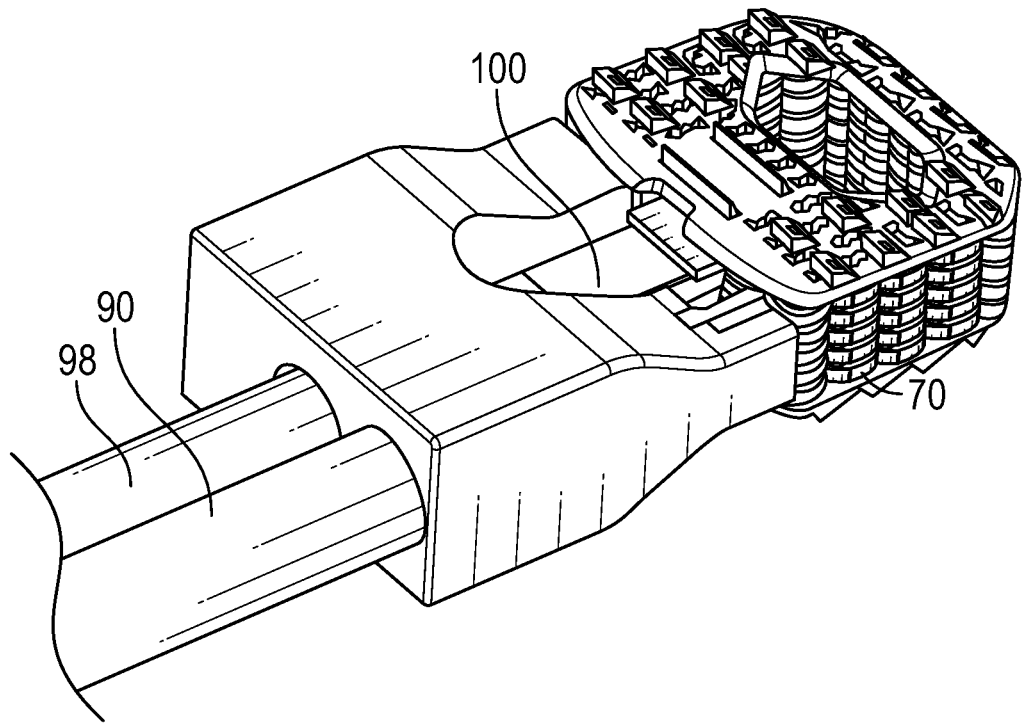
FIG. 29 shows a perspective view of an anchor-deployment tool inserted into an anchor cavity of an embodiment of an implant prior to deployment of the anchors.
Figure 30:
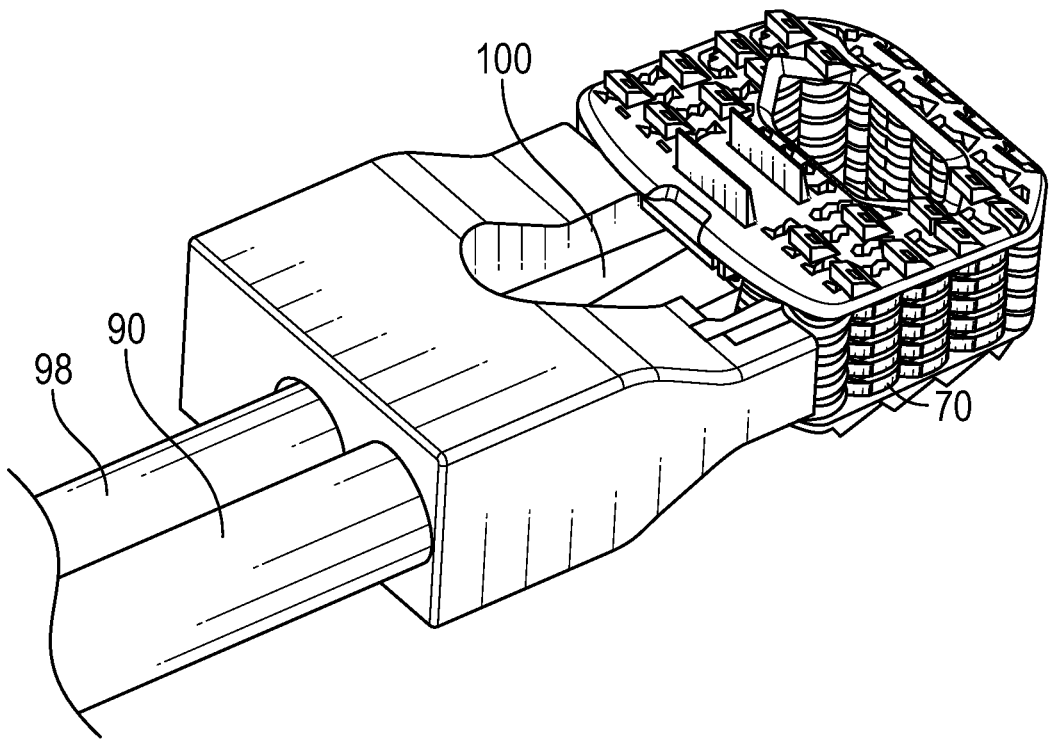
FIG. 30 shows a perspective view of the anchor-deployment tool of FIG. 29 after the anchor-deployment tool has been manipulated to deploy the anchors of the embodiment of an implant of FIG. 29.

After the implant is positioned in the disc space the anchors 62 are deployed into the adjacent spinal endplates with a 0° profile deployment method. In other words, the anchors 62 are deployable with use of an instrument engaging the implant directly anterior to the implant. A shaft 98 with a flat-headed end 100 is passed through the inserter 90 (FIG. 28) and into the implant (FIG. 29). The shaft is then rotated until the anchors 62 are deployed (FIG. 30).

Embodiments of the invention provide orthopedic implants, particularly implemented in the current examples as interbody spacers, the implants having a combination of correct pore size and stiffness/flexibility. Embodiments of the invention also provide methods for producing such orthopedic implants. When the implants have the proper pore size and stiffness, osteocytes are able to properly bridge the pores of the implant and then experience a proper compressive load to stimulate the bone cells to form bone within the pores throughout the implants according to Wolff's law.

According to embodiments of the invention, an implant includes a body formed of an osteoconductive material. The body may have a stiffness of between 400 megapascals (MPa) and 1,200 MPa. Additionally, the body may include a plurality of pores having an average size of between 150 microns and 600 microns. The pores may be interconnected and permit the growth of bone therein. The implant may be an interbody spacer.

The osteoconductive material may be any of a variety of materials such as titanium, tantalum, and alloys thereof or titanium and alloys thereof such as, for example Ti 6-4 (approximately 6% aluminum, 4% vanadium, up to 0.25% iron, up to 0.2% oxygen and the remainder titanium) and other recognized alloys used for implants. Alternatively, the osteoconductive material may be any material now known or later discovered to be biocompatible and osteoconductive and providing characteristics in line with those discussed herein. In certain embodiments, the implant has a stiffness of between 600 MPa and 1,000 MPa. In other embodiments, the implant has a stiffness of between 750 MPa and 850 MPa. In still other embodiments, the implant has a stiffness of between 950 MPa and 1,050 MPa. In additional embodiments, the implant has a stiffness of between 750 MPa and 1,050 MPa.

The implant may be manufactured using an additive manufacturing process. The implant may have a coil spring construction. The coil spring construction may have a vertical spacing between coils of between 250 microns and 350 microns. The coil spring construction may have a coil diameter of between 400 microns and 600 microns. The implant may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

According to alternate embodiments of the invention, an implant includes a body comprising a plurality of coil springs formed of an osteoconductive material. The body may have a stiffness of between 400 MPa and 1,200 MPa. The body may also include a plurality of pores having an average size of between 150 microns and 600 microns.

The osteoconductive material may be any of a variety of materials such as titanium, tantalum, and alloys thereof or titanium and alloys thereof. Alternatively, the osteoconductive material may be any material now known or later discovered to be biocompatible and osteoconductive and providing characteristics in line with those discussed herein. In certain embodiments, the implant has a stiffness of between 600 MPa and 1,000 MPa. In other embodiments, the implant has a stiffness of between 750 MPa and 850 MPa. In still other embodiments, the implant has a stiffness of between 950 MPa and 1,050 MPa. In additional embodiments, the implant has a stiffness of between 750 MPa and 1,050 MPa.

The implant may be manufactured using an additive manufacturing process. The coil springs of the body may have a vertical spacing between coils of between 250 microns and 350 microns. The coil springs of the body may have a coil diameter of between 400 microns and 600 microns. The implant may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

According to alternate embodiments of the invention, an implant includes a body comprising a plurality of coil springs manufactured using an additive manufacturing process. The coil springs may be arranged into a plurality of overlapping coil packs having coils that are connected and coils that are intertwined without connecting. The coil springs may include coils having a clockwise sweep direction and coils having a counterclockwise sweep direction. The body may have a stiffness of between 400 MPa and 1,200 MPa. The body may have a plurality of pores having an average size of between 150 microns and 600 microns.

The osteoconductive material may be any of a variety of materials such as titanium, tantalum, and alloys thereof or titanium and alloys thereof. Alternatively, the osteoconductive material may be any material now known or later discovered to be biocompatible and osteoconductive and providing characteristics in line with those discussed herein. In certain embodiments, the implant has a stiffness of between 600 MPa and 1,000 MPa. In other embodiments, the implant has a stiffness of between 750 MPa and 850 MPa. In still other embodiments, the implant has a stiffness of between 950 MPa and 1,050 MPa. In additional embodiments, the implant has a stiffness of between 750 MPa and 1,050 MPa.

The coil springs of the body may have a vertical spacing between coils of between 250 microns and 350 microns. The coil springs of the body may have a coil diameter of between 400 microns and 600 microns. The implant may have a nested coil spring construction.

According to further embodiments of the invention, a method of manufacturing an implant includes a step of forming an implant body using an additive manufacturing process. The step of forming an implant body may include forming a plurality of coils of a biocompatible material or an osteoconductive material. The coils so formed may have a vertical coil spacing and a coil diameter chosen to impart certain physical characteristics to the implant while facilitating use of the additive manufacturing process. The implant body so formed may have a stiffness of between 400 MPa and 1,200 MPa, and may include a plurality of pores having an average size of between 150 microns and 600 microns.

In certain embodiments, the implant body so formed has a stiffness of between 600 MPa and 1,000 MPa. In other embodiments, the implant body so formed has a stiffness of between 750 MPa and 850 MPa. In still other embodiments, the implant body so formed has a stiffness of between 950 MPa and 1,050 MPa. In additional embodiments, the implant body so formed has a stiffness of between 750 MPa and 1,050 MPa.

The coil springs of the body may have a vertical spacing between coils of between 250 microns and 350 microns. The coil springs of the body may have a coil diameter of between 400 microns and 600 microns. The implant may have a nested coil spring construction.

The implant so formed may have a nested coil spring construction. The implant may also or alternatively have a plurality of overlapping coil packs. Where present, the plurality of overlapping coil packs may include coils that are connected and coils that are intertwined without connecting. The implant may have a plurality of coil springs joined in clockwise to counter-clockwise sweep directions.

As discussed above, it would be ideal for an implant to provide porosity and stiffness generally similar to actual bone using materials that are conducive to bone growth. In addition to an ideal pore size of 150 microns to 650 microns, an ideal implant would have a stiffness of between 400 MPa and 1.2 gigapascals (GPa) (1,200 MPa). Additionally, when pores are at the larger end of the ideal range, the implant will allow for the fastest and greatest extent of vascularization. Bones that experience larger loads generally have smaller pores and greater stiffness. To grow denser, stronger bone requires an implant with upper-range pore sizes and lower-range stiffness to allow the bone to experience more of the load. In this way, the implant avoids shielding bone within the implant from stress that would cause the bone to grow. Additionally, the larger pores allow the bone to better occupy the available space.

Embodiments of the invention provide implants having the desired stiffness and pore size ranges while still providing for enhanced fixation capabilities as discussed herein.

The present invention may be embodied in other specific forms without departing from its spirit or essential characteristics. The described embodiments are to be considered in all respects only as illustrative and not restrictive. The scope of the invention is, therefore, indicated by the appended claims, rather than by the foregoing description. All changes which come within the meaning and range of equivalency of the claims are to be embraced within their scope.

What is claimed and desired to be secured by Letters Patent is:

1. An implant comprising anchors deployable via a 0° profile deployment method, wherein the implant comprises a flexible beam adapted to be flexibly displaced from a resting position by placement of one of the anchors within the implant, and wherein when said one of the anchors is deployed, the flexible beam returns to the resting position and prevents said one of the anchors from leaving its deployed position.

2. The implant as recited in claim 1, wherein the anchors are deployable generally orthogonally to a plane of insertion of the implant.

3. The implant as recited in claim 1, wherein the anchors are deployable within 10° of orthogonal to a plane of insertion of the implant.

4. The implant as recited in claim 1, wherein the anchors each comprise a pair of blades extending generally orthogonally away from a base.

5. The implant as recited in claim 4, wherein the implant comprises two anchors, one deployable through a cranial surface of the implant and one deployable through a caudal surface of the implant, and wherein the implant comprises four flexible beams, two flexible beams per anchor serving to prevent that anchor from leaving its deployed position.

6. The implant as recited in claim 5, wherein the anchors are deployable by inserting a flat blade between the anchors and by twisting the flat blade to force the anchors apart.

7. The implant as recited in claim 1, further comprising:
an inserter-engagement opening formed in a body of the implant and adapted to be engaged by an inserter during implantation of the implant; and
an anchor cavity housing the anchors.

8. The implant as recited in claim 7, wherein the anchor cavity contains two opposed anchors, a first anchor adapted to extend in a cranial direction through one or more slots in a cranial surface of the implant, and a second anchor adapted to extend in a caudal direction through one or more slots in a caudal surface of the implant.

9. An implant comprising anchors deployable via a 0° profile deployment method, wherein the implant comprises a body formed of a biocompatible material, the body comprises a stiffness of between 400 megapascals (MPa) and 1,200 MPa, and the body comprises a plurality of pores having an average size of between 150 microns and 600 microns.

10. The implant as recited in claim 9, wherein the implant body comprises a coil spring construction.

11. The implant as recited in claim 9, wherein the implant body comprises a nested coil spring construction.

12. The implant as recited in claim 9, wherein the body comprises a plurality of overlapping coil packs.

13. An implant comprising:
a body adapted to be inserted into an interbody space between two vertebral bodies of a human spine, the body comprising:
a cranial surface adapted to rest against one of the vertebral bodies; and
a caudal surface adapted to rest against the other of the vertebral bodies;
an inserter-engagement opening formed in the body;
an anchor cavity with a pair of two-bladed anchors disposed therein; and
a flexible beam adapted to be flexibly displaced from a resting position by placement of one of the anchors within the implant, and wherein when said one of the anchors is deployed, the flexible beam returns to the resting position and prevents said one of the anchors from leaving its deployed position;
wherein the anchors are adapted to be deployable through slots in the cranial surface and in the caudal surface to engage with the vertebral bodies to fix the implant in the interbody space.

14. The implant as recited in claim 13, wherein the anchors each comprise a pair of blades extending generally orthogonally away from a base.

15. The implant as recited in claim 13, wherein the body comprises four flexible beams serving to engage the anchors in a fully-deployed position such that the anchors are prevented from leaving the fully-deployed position.

16. The implant as recited in claim 13, wherein the anchors are deployable by inserting a flat blade between the anchors and by twisting the flat blade to force the anchors apart.

17. The implant as recited in claim 16, wherein the flat blade may be inserted between the anchors and twisted while remaining entirely within an anterior axis of the implant.

18. The implant as recited in claim 13, wherein the inserter-engagement opening is formed by adjacent coil packs sweeping into each other to form a detent with no solid external geometry that would alter a stiffness of the body.

19. The implant as recited in claim 18, wherein the detent forms a void adapted to engage tabs of an inserter device.

20. An implant comprising:
- a body adapted to be inserted into an interbody space between two vertebral bodies of a human spine, the body comprising:
  - a cranial surface adapted to rest against one of the vertebral bodies; and
  - a caudal surface adapted to rest against the other of the vertebral bodies;
- an inserter-engagement opening formed in the body; and
- an anchor cavity with a pair of two-bladed anchors disposed therein;
- wherein the anchors are adapted to be deployable through slots in the cranial surface and in the caudal surface to engage with the vertebral bodies to fix the implant in the interbody space; and
- wherein the implant comprises a body formed of a biocompatible material, the body comprises a stiffness of between 400 megapascals (MPa) and 1,200 MPa, and the body comprises a plurality of pores having an average size of between 150 microns and 600 microns.

* * * * *